(12) United States Patent
Liu et al.

(10) Patent No.: US 10,611,774 B2
(45) Date of Patent: Apr. 7, 2020

(54) SALT FORM OF DPPIV INHIBITOR AND PREPARATION METHOD THEREOF

(71) Applicant: SHANGHAI INSTITUTE OF MATERIA MEDICA, CHINESE ACADEMY OF SCIENCES, Shanghai (CN)

(72) Inventors: Hong Liu, Shanghai (CN); Jiang Wang, Shanghai (CN); Jian Li, Shanghai (CN); Jia Li, Shanghai (CN); Jingya Li, Shanghai (CN); Hualiang Jiang, Shanghai (CN); Xiaomin Luo, Shanghai (CN); Kaixian Chen, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 16/087,318

(22) PCT Filed: Mar. 22, 2017

(86) PCT No.: PCT/CN2017/077679
§ 371 (c)(1),
(2) Date: Oct. 11, 2018

(87) PCT Pub. No.: WO2017/162168
PCT Pub. Date: Sep. 28, 2017

(65) Prior Publication Data
US 2019/0031678 A1    Jan. 31, 2019

(30) Foreign Application Priority Data

Mar. 22, 2016 (CN) .......................... 2016 1 0165573

(51) Int. Cl.
*A61K 31/519* (2006.01)
*C07D 495/04* (2006.01)
*A61P 3/10* (2006.01)

(52) U.S. Cl.
CPC .............. *C07D 495/04* (2013.01); *A61P 3/10* (2018.01); *C07B 2200/13* (2013.01)

(58) Field of Classification Search
CPC .......................... A61K 31/519; C07D 495/04
USPC ......................................... 514/260.1; 544/278
See application file for complete search history.

(56) References Cited

U.S. PATENT DOCUMENTS 9,045,491 B2 * 6/2015 Liu ...................... C07D 495/04

FOREIGN PATENT DOCUMENTS

| WO | 2010072776 A1 | 7/2010 |
| WO | 2013078765 A1 | 6/2013 |
| WO | 2016127898 A1 | 8/2016 |

OTHER PUBLICATIONS

Int'l Search Report dated Jun. 20, 2017 in Int'l Application No. PCT/CN2017/077679.

* cited by examiner

*Primary Examiner* — Jeffrey H Murray
(74) *Attorney, Agent, or Firm* — Panitch Schwarze Belisario & Nadel LLP

(57) ABSTRACT

The invention relates to a salt form of (R)-methyl-2-(3-aminopiperidin-1-yl)-3-(2-cyanobenzyl)-4-carbonyl-3,4-dihydrothiophene[3,2-d]pyrimidine-6-carboxylic acid and a preparation method for the salt form. Also disclosed is a pharmaceutical composition of the formula I compound salt form. The salt form of the invention provides powerful in vivo hypoglycemic activity and is expected to be a novel pharmaceutical active ingredient for treating or preventing diabetes mellitus type 2 and/or complications of diabetes mellitus type 2

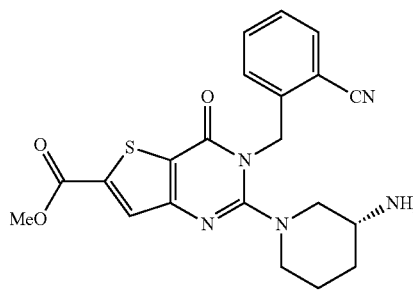

I

18 Claims, 16 Drawing Sheets

SALT FORM OF DPPIV INHIBITOR AND PREPARATION METHOD THEREOF

CROSS-REFERENCE TO RELATED APPLICATION

This application is a Section 371 of International Application No. PCT/CN2017/077679, filed Mar. 22, 2017, which was published in the Chinese language on Sep. 28, 2017, under International Publication No. WO 2017/162168 A1, which claims priority under 35 U.S.C. § 119(b) to Chinese Patent Application No. 201610165573.9, filed on Mar. 22, 2016, the disclosures of which are incorporated herein by reference in their entireties.

TECHNICAL FIELD

The present invention relates to the field of medicinal chemistry, and in particular to a salt form of (R)-methyl-2-(3-aminopiperidin-1-yl)-3-(2-cyanobenzyl)-4-carbonyl-3,4-dihydrothiophene [3,2-d]pyrimidine-6-carboxylic acid, preparation method and use thereof.

BACKGROUND ART

Diabetes is a metabolic disease caused by metabolic disorders of sugar, fat and protein which are resulted from insufficient insulin secretion in the human body and dysfunction of pancreatic β cells. Hyperglycemia caused by diabetes can cause damage of body tissues and lead to microvascular lesion and macrovascular lesion, such as retinopathy, kidney disease, neuropathy, stroke and coronary atheroma, and other complications that seriously damage human health and threaten human life safety.

Diabetes can be divided into type 1 diabetes (T1DM) and type 2 diabetes (T2DM). The DPP-IV inhibitor (saxagliptin) improves alpha and beta cell dysfunction by increasing the levels of endogenous active glucagon-like peptide-1 (GLP-1) and glucose-dependent insulinotropic peptide (GIP). DPP IV inhibitors can significantly reduce blood glucose levels in the body, increase glucose tolerance, promote insulin secretion, reduce glucagon levels, delay insulin resistance and increase response level of insulin in patients with type 2 diabetes when blood glucose increases. Compared with existing oral diabetes drugs, DPP IV inhibitors have following characteristics: (1) DPP IV inhibitors do not require injections, and can continuously reduce glycosylated hemoglobin levels by oral administration; (2) long-term use of DPP IV inhibitors have good tolerance; (3) insulin secretion and the release of glucagon can be improved; (4) insulin sensitivity can be improved, while increasing pancreatic β cell function; (5) incidence of hypoglycemia is lower, and weight gain, nausea, vomiting and gastrointestinal dysfunction won't occur; (6) DPP IV inhibitors have synergistic effects when used in combination with other type II diabetes drugs. However, such drugs may cause side effects such as pancreatitis, urticaria and angioedema.

(R)-methyl-2-(3-aminopiperidin-1-yl)-3-(2-cyanobenzyl)-4-carbonyl-3,4-dihy drothiophene[3,2-d]pyrimidine-6-carboxylic acid (compound of formula I) is a novel DPP IV inhibitor with strong hypoglycemic activity in vivo. However, the overall performance of the existing (R)-methyl-2-(3-aminopiperidin-1-yl)-3-(2-cyanobenzyl)-4-carbonyl-3,4-dihydrothiophene[3,2-d]pyrimidine-6-carboxylic acid is still unsatisfactory.

Therefore, there is an urgent need in the art to develop a new salt form of (R)-methyl-2-(3-aminopiperidin-1-yl)-3-(2-cyanobenzyl)-4-carbonyl-3,4-dihydrothiophene[3,2-d]pyrimidine-6-carboxylic acid which is highly efficient, low toxicity and long-acting so as to obtain a pharmaceutically active ingredient having superior properties.

SUMMARY OF THE INVENTION

It is an object of the present invention to provide salt forms of a compound of formula I which is highly effective, low toxicity and long lasting.

In the first aspect of the invention, a salt form of a compound of formula I is provided, and the salt form is selected from the group consisting of hydrochloride, maleate, phosphate and glycolate

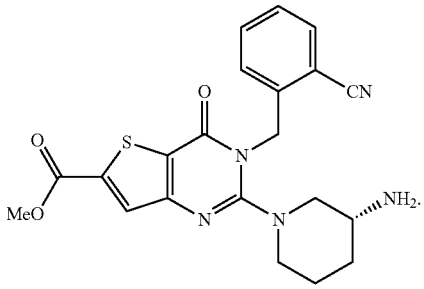

I

In another preferred embodiment, the salt form is a crystal.

In another preferred embodiment, the hydrochloride is a crystal.

In another preferred embodiment, the X-ray powder diffraction pattern of the hydrochloride crystal includes 3 or more 2θ values selected from the group consisting of: 7.43±0.2°, 11.06±0.2°, 11.70±0.2°, 13.46±0.2°, 15.03±0.2°, 15.34±0.2°, 18.32±0.2°, 21.96±0.2°, 24.01±0.2°, 27.20±0.2°, 29.32±0.2°, 30.26±0.2°.

In another preferred embodiment, the X-ray powder diffraction pattern of the hydrochloride crystal includes 3 or more 2θ values selected from the group consisting of 7.43°, 11.06°, 11.70°, 18.32°, 21.96°, 24.01°, 27.20°, 29.32°, 30.26°.

In another preferred embodiment, the X-ray powder diffraction pattern of the hydrochloride crystal includes 3 or more 2θ values selected from the group consisting of: 7.43±0.2°, 11.06±0.2°, 11.70±0.2°, 13.46±0.2°, 15.03±0.2°, 15.34±0.2°, 15.84±0.2°, 16.35±0.2°, 17.59±0.2°, 18.32±0.2°, 19.54±0.2°, 20.13±0.2°, 21.24±0.2°, 21.96±0.2°, 22.46±0.2°, 22.74±0.2°, 23.67±0.2°, 24.01±0.2°, 24.83±0.2°, 25.19±0.2°, 26.63±0.2°, 27.20±0.2°, 29.32±0.2°, 30.26±0.2°, 32.15±0.2°.

In another preferred embodiment, the X-ray powder diffraction pattern of the hydrochloride crystal is substantially characterized as in FIG. 1.

In another preferred embodiment, the X-ray powder diffraction pattern of the hydrochloride crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the hydrochloride crystal, there is no melting peak prior to decomposition.

In another preferred embodiment, the DSC spectrum of the hydrochloride crystal is substantially as shown in FIG. 3.

In another preferred embodiment, in the TG pattern of the hydrochloride crystal, there is a characteristic absorption peak at 272±2° C.

In another preferred embodiment, in the TG pattern of the hydrochloride crystal, there is a characteristic absorption peak at 272.6° C.

In another preferred embodiment, the thermogravimetric analysis pattern (TG pattern) of the hydrochloride crystal is substantially characterized as in FIG. 2.

In another preferred embodiment, the thermal weight loss of the hydrochloride crystal is 64-65 wt % at 400° C., preferably 64.33 wt %.

In another preferred embodiment, the weight gain of the hydrochloride crystal is calculated to be ≤3%, preferably ≤1%, more preferably ≤0.3%, after being placed in a desiccator having a humidity of 50% for 24 hours and taken out.

In another preferred embodiment, the DVS pattern of the hydrochloride crystal is substantially as shown in FIG. 4.

In another preferred embodiment, the IR pattern of the hydrochloride crystal includes 3 or more characteristic absorption peaks represented by the wavelength λ selected from the group consisting of: 3429±2 cm$^{-1}$, 2951±2 cm$^{-1}$, 2827±2 cm$^{-1}$, 2225±2 cm$^{-1}$, 1720±2 cm$^{-1}$, 1687±2 cm$^{-1}$, 1560±2 cm$^{-1}$, 1533±2 cm$^{-1}$, 1446±2 cm$^{-1}$, 1385±2 cm$^{-1}$, 1261±2 cm$^{-1}$, 1064±2 cm$^{-1}$, 771±2 cm$^{-1}$.

In another preferred embodiment, the IR pattern of the hydrochloride crystal is substantially as shown in FIG. 5.

In another preferred embodiment, the Raman diagram of the hydrochloride crystal is substantially as shown in FIG. 6.

In another preferred embodiment, the maleate is a crystal.

In another preferred embodiment, the X-ray powder diffraction pattern of the maleate crystal includes 3 or more 2θ values selected from the group consisting of 7.55±0.2°, 12.41±0.2°, 15.45±0.2°, 17.50±0.2°, 20.89±0.2°, 26.59±0.2°, 26.93±0.2°.

In another preferred embodiment, the X-ray powder diffraction pattern of the maleate crystal includes 3 or more 2θ values selected from the group consisting of 7.55±0.2°, 12.41±0.2°, 15.45±0.2°, 17.50±0.2°, 20.89±0.2°, 26.59±0.2°, 26.93±0.2°, 27.10±0.2°, 28.21±0.2°, 30.53±0.2°, 32.96±0.20°.

In another preferred embodiment, the X-ray powder diffraction pattern of the maleate crystal includes 3 or more 2θ values selected from the group consisting of 7.55±0.2°, 10.83±0.2°, 12.41±0.2°, 13.22±0.2°, 14.38±0.2°, 14.75±0.2°, 15.45±0.2°, 15.80±0.2°, 17.50±0.2°, 18.30±0.2°, 19.40±0.2°, 20.43±0.2°, 20.89±0.2°, 21.85±0.2°, 22.87±0.2°, 23.25±0.2°, 25.04±0.2°, 26.59±0.2°, 26.93±0.2°, 27.10±0.2°, 28.21±0.2°, 30.53±0.2°, 32.96±0.20°.

In another preferred embodiment, the X-ray powder diffraction pattern of the maleate crystal is substantially characterized as in FIG. 7.

In another preferred embodiment, the X-ray powder diffraction pattern of the maleate crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the maleate crystal, there is a characteristic absorption peak at 113±5° C.

In another preferred embodiment, in the differential scanning calorimetry analysis spectrum (DSC spectrum) of the maleate crystal, there is a characteristic absorption peak at 113.8° C.

In another preferred embodiment, the DSC pattern of the maleate crystal is substantially as shown in FIG. 9.

In another preferred embodiment, the TG pattern of the maleate crystal comprises a characteristic absorption peak selected from the group consisting of 77±2° C., 180±5° C. and 284±5° C.

In another preferred embodiment, the TG pattern of the maleate crystal comprises a characteristic absorption peak selected from the group consisting of 77.3° C., 179.6° C. and 283.6° C.

In another preferred embodiment, the thermogravimetric analysis pattern (TG pattern) of the maleate crystal is substantially characterized as in FIG. 8.

In another preferred embodiment, the thermal weight loss of the maleate crystal is 42-43 wt % at 400° C., preferably 42.58 wt %.

In another preferred embodiment, the starting value of the endothermic transition temperature of the maleate crystal is 110±2° C., preferably 110.37° C.

In another preferred embodiment, the weight gain of the maleate crystal is calculated to be ≤3%, preferably ≤1%, more preferably ≤0.3%, after being placed in a desiccator having a humidity of 50% for 24 hours and taken out.

In another preferred embodiment, the DVS pattern of maleate crystal is substantially as shown in FIG. 10.

In another preferred embodiment, the IR pattern of the maleate comprises 3 or more characteristic absorption peaks represented by the wavelength λ selected from the group consisting of: 3429±2 cm$^{-1}$, 3062±2 cm$^{-1}$, 2954±2 cm$^{-1}$, 2862±2 cm$^{-1}$, 2224±2 cm$^{-1}$, 1720±2 cm$^{-1}$, 1676±2 cm$^{-1}$, 1558±2 cm$^{-1}$, 1531±2 cm$^{-1}$, 1469±2 cm$^{-1}$, 1354±2 cm$^{-1}$, 1290±2 cm$^{-1}$, 1219±2 cm$^{-1}$, 1063±2 cm$^{-1}$, 864±2 cm$^{-1}$, 775±2 cm$^{-1}$, 654±2 cm$^{-1}$.

In another preferred embodiment, the IR pattern of the maleate crystal is substantially as shown in FIG. 11.

In another preferred embodiment, the Raman diagram of the maleate crystal is substantially as shown in FIG. 12.

In another preferred embodiment, the phosphate is a crystal.

In another preferred embodiment, the X-ray powder diffraction pattern of the phosphate crystal comprises 3 or more 2θ values selected from the group consisting of 11.99±0.2°, 12.20±0.2°, 14.80±0.2°, 20.11±0.2°, 20.46±0.2°, 24.18±0.2°, 24.68±0.2°.

In another preferred embodiment, the X-ray powder diffraction pattern of the phosphate crystal comprises 3 or more 2θ values selected from the group consisting of 11.99±0.2°, 12.20±0.2°, 14.80±0.2°, 20.11±0.2°, 20.46±0.2°, 23.15±0.2°, 24.18±0.2°, 24.68±0.2°, 25.63±0.2°, 26.15±0.2°.

In another preferred embodiment, the X-ray powder diffraction pattern of the phosphate crystal comprises 3 or more 2θ values selected from the group consisting of 6.23±0.2°, 11.99±0.2°, 12.20±0.2°, 14.80±0.2°, 15.16±0.2°, 16.04±0.2°, 16.56±0.2°, 17.90±0.2°, 20.11±0.2°, 20.46±0.2°, 22.74±0.2°, 23.15±0.2°, 24.18±0.2°, 24.68±0.2°, 25.63±0.2°, 26.15±0.2°.

In another preferred embodiment, the X-ray powder diffraction pattern of the phosphate crystal is substantially characterized as in FIG. 13.

In another preferred embodiment, the X-ray powder diffraction pattern of the phosphate crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the phosphate crystal, there is a characteristic absorption peak at 155±5° C., preferably 154.8° C.

In another preferred embodiment, the DSC pattern of the phosphate crystal is substantially as shown in FIG. 15.

In another preferred embodiment, in the TG pattern of the phosphate crystal, there is a characteristic absorption peak at 361±2° C., preferably 361.0° C.

In another preferred embodiment, the thermal weight loss of the phosphate crystal is 47-48 wt % at 400° C., preferably 47.57 wt %.

In another preferred embodiment, the thermogravimetric analysis pattern (TG pattern) of the phosphate crystal is substantially characterized as in FIG. 14.

In another preferred embodiment, the starting value of the endothermic transition temperature of the phosphate crystal is 148±2° C., preferably 148.0° C.

In another preferred embodiment, the weight gain of the phosphate crystal is calculated to be ≤3%, preferably ≤1%, more preferably ≤0.3%, after being placed in a desiccator having a humidity of 50% for 24 hours and taken out.

In another preferred embodiment, the DVS pattern of the phosphate crystal is substantially as shown in FIG. 16.

In another preferred embodiment, the IR pattern of the phosphate crystal comprises 3 or more characteristic absorption peaks represented by the wavelength λ selected from the group consisting of: 3408±2 $cm^{-1}$, 2951±2 $cm^{-1}$, 2860±2 $cm^{-1}$, 2225±2 $cm^{-1}$, 1716±2 $cm^{-1}$, 1684±2 $cm^{-1}$, 1601±2 $cm^{-1}$, 1556±2 $cm^{-1}$, 1531±2 $cm^{-1}$, 1450±2 $cm^{-1}$, 1379±2 $cm^{-1}$, 1282±2 $cm^{-1}$, 1238±2 $cm^{-1}$, 1124±2 $cm^{-1}$, 1064±2 $cm^{-1}$, 947±2 $cm^{-1}$, 868±2 $cm^{-1}$, 758±2 $cm^{-1}$, 521±2 $cm^{-1}$.

In another preferred embodiment, the IR pattern of the phosphate crystal is substantially as shown in FIG. 17.

In another preferred embodiment, the Raman diagram of the phosphate crystal is substantially as shown in FIG. 18.

In another preferred embodiment, the glycolate is a crystal.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°, 20.51±0.2°, 21.22±0.2°, 21.78±0.2°, 23.00±0.2°.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°, 20.51±0.2°, 21.22±0.2°, 21.78±0.2°, 23.00±0.2°, 23.87±0.2°, 24.08±0.2°, 24.37±0.2°, 25.52±0.2°, 33.81±0.2°.

In another preferred embodiment, the X-ray powder diffraction pattern of the glycolate crystal includes 3 or more 2θ values selected from the group consisting of 6.66±0.2°, 8.92±0.2°, 9.91±0.2°, 10.20±0.2°, 13.35±0.2°, 13.92±0.2°, 15.78±0.2°, 16.71±0.2°, 16.89±0.2°, 17.41±0.2°, 18.70±0.2°, 19.37±0.2°, 20.12±0.2°, 20.51±0.2°, 21.22±0.2°, 21.78±0.2°, 22.75±0.2°, 23.00±0.2°, 23.87±0.2°, 24.08±0.2°, 24.37±0.2°, 25.52±0.2°, 26.44±0.2°, 27.02±0.2°, 27.48±0.2°, 28.23±0.2°, 28.63±0.2°, 28.84±0.2°, 29.68±0.2°, 30.14±0.2°, 30.51±0.2°, 31.41±0.2°, 31.76±0.2°, 33.00±0.2°, 33.81±0.2°, 34.13±0.2°, 35.21±0.2°, 25.83±0.2°, 36.37±0.2°, 37.70±0.2°, 37.93±0.2°.

In another preferred embodiment, the X-ray powder diffraction pattern of the glycolate crystal is substantially characterized as in FIG. 19.

In another preferred embodiment, the X-ray powder diffraction pattern of the glycolate crystal has a deviation of ±0.5° from the characteristic absorption peak represented by the 2θ value, preferably a deviation of ±0.3°, more preferably a deviation of ±0.1°.

In another preferred embodiment, in the differential scanning calorimetry analysis spectrum (DSC spectrum) of the glycolate crystal, there is a characteristic absorption peak at 189±5° C.

In another preferred embodiment, the DSC pattern of the glycolate crystal is substantially as shown in FIG. 21.

In another preferred embodiment, the starting value of the endothermic transition temperature of the glycolate crystal is 148±2° C., preferably 148.0° C.

In another preferred embodiment, in the TG pattern of the glycolate crystal, there is a characteristic absorption peak at 192±2° C. and 268±2° C., preferably 192.5° C., 268.0° C.

In another preferred embodiment, the TG pattern of the glycolate crystal is substantially as shown in FIG. 20.

In another preferred embodiment, the thermal weight loss of the glycolate crystal is 53-54 wt % at 400° C., preferably 53.41 wt %.

In another preferred embodiment, the weight gain of the glycolate crystal is calculated to be ≤3%, preferably ≤1%, more preferably ≤0.3%, after being placed in a desiccator having a humidity of 50% for 24 hours and taken out.

In another preferred embodiment, the DVS pattern of glycolate crystal is substantially as shown in FIG. 22.

In another preferred embodiment, the IR pattern of the glycolate crystal includes 3 or more characteristic absorption peaks represented by the wavelength λ selected from the group consisting of 3462±2 $cm^{-1}$, 2958±2 $cm^{-1}$, 2837±2 $cm^{-1}$, 2227±2 $cm^{-1}$, 1720±2 $cm^{-1}$, 1674±2 $cm^{-1}$, 1558±2 $cm^{-1}$, 1533±2 $cm^{-1}$, 1450±2 $cm^{-1}$, 1350±2 $cm^{-1}$, 1282±2 $cm^{-1}$, 1223±2 $cm^{-1}$, 1072±2 $cm^{-1}$, 928±2 $cm^{-1}$, 760±2 $cm^{-1}$, 692±2 $cm^{-1}$.

In another preferred embodiment, the IR pattern of the glycolate is substantially as shown in FIG. 23.

In another preferred embodiment, the Raman diagram of the glycolate is substantially as shown in FIG. 24.

In the second aspect of the present invention, a salt form combination is provided, the salt form combination comprises one or more salt forms of the hydrochloride, the maleate, the phosphate, the glycolate or the like according to the first aspect of the present invention or consists of salt forms of the hydrochloride, the maleate, the phosphate or the glycolate according to the first aspect of the invention.

In another preferred embodiment, by the total weight of the salt form combination, the total weight percentage of the hydrochloride, the maleate, the phosphate and the glycolate is 60-99.999%, preferably 80-99.999%, more preferably 90-99.999%.

In another preferred embodiment, the salt form combination further comprises: other salt forms of (R)-methyl-2-(3-aminopiperidin-1-yl)-3-(2-cyanobenzyl)-4-carbonyl-3,4-dihydrothiophene [3,2-d]pyrimidine-6-carboxylic acid, free base of (R)-methyl-2-(3-aminopiperidin-1-yl)-3-(2-cyanobenzyl)-4-carbonyl-3,4-dihydrothiophene[3,2-d]pyrimidine-6-carboxylic acid.

In the third aspect of the invention, a method for preparing a salt form of a compound of formula I according to the first aspect of the invention is provided, and the method comprises the following steps of:

(1) a free base of the compound of formula I is dissolved in a solvent and a certain amount of acid is added;

(2) the solution obtained in step (1) is allowed to be placed for a certain period of time to carry out a reaction at a certain temperature, and crystals are crystallized with stirring to obtain solids;

(3) the solids obtained in step (2) are filtered and/or dried to obtain the salt form of the first aspect of the invention.

In another preferred embodiment, in step (1), the solvent is selected from the group consisting of a alcohol, ether, ketone, ester, or a combination thereof.

In another preferred embodiment, the alcohol is a C1-C10 alcohol, preferably C1-C8 alcohol, more preferably C1-C5 alcohol.

In another preferred embodiment, the alcohol is selected from the group consisting of methanol, ethanol, n-propanol, isopropanol, n-butanol, neopentyl alcohol, or a combination thereof.

In another preferred embodiment, the ether is a C2-C8 ether, preferably a C2-C5 ether.

In another preferred embodiment, the ether is selected from the group consisting of ethyl ether, tetrahydrofuran, or a combination thereof.

In another preferred embodiment, the ester is C1-C10 ester, preferably C1-C7 ester, more preferably C1-C5 ester.

In another preferred embodiment, the ester is selected from the group consisting of methyl formate, ethyl acetate, isobutyl formate, or a combination thereof.

In another preferred embodiment, in step (1), the molar ratio of the free base to the acid is 1:0.8-1:1.5, preferably 1:0.9-1:1.3, more preferably 1:1.0-1:1.1.

In another preferred embodiment, in step (1), the temperature ranges from 10 to 80° C., preferably from 30 to 50° C.

In another preferred embodiment, in step (1), the reaction time is from 0.1 to 10 h, preferably from 0.5 to 6 h.

In another preferred embodiment, in step (2), the drying temperature is from 10 to 90° C., preferably from 20 to 80° C., more preferably from 40 to 70° C.

In another preferred embodiment, in step (2), the drying pressure is 0 to 20 KPa, preferably 0 to 10 KPa, more preferably 5 to 10 KPa.

In another preferred embodiment, in step (2), the drying time is from 5 to 150 hours, preferably from 30 to 100 hours, more preferably from 60 to 80 hours.

In another preferred embodiment, in step (2), the crystallization is carried out at 0 to 50° C., preferably 0 to 40° C., more preferably 20 to 30° C.

In another preferred embodiment, the crystallization is carried out with stirring.

In another preferred embodiment, in step (3), the yield of the method is from 50% to 99.9%, preferably from 75% to 99.9%, more preferably from 85% to 99.9%.

In the fourth aspect of the invention, a pharmaceutical composition is provided, and the pharmaceutical composition comprises:

(1) the hydrochloride, the maleate, the phosphate, the glycolate of the compound of formula I according to the first aspect of the invention, or a combination thereof;

(2) a pharmaceutically acceptable excipient.

In another preferred embodiment, the excipient is selected from the group consisting of fillers, disintegrants, binders, lubricants, or a combination thereof.

In another preferred embodiment, the filler is selected from the group consisting of starch, lactose, microcrystalline cellulose, dextrin, mannitol, magnesium oxide, calcium sulfate, or a combination thereof.

In another preferred embodiment, the disintegrant is selected from the group consisting of carboxymethylcellulose and a salt thereof, crosslinked carboxymethylcellulose and a salt thereof, crosslinked povidone, sodium carboxymethyl starch, low substituted hydroxypropylcellulose, or a combination thereof.

In another preferred embodiment, the binder is selected from the group consisting of povidone, hydroxypropylmethylcellulose, starch pulp, or a combination thereof.

In another preferred embodiment, the lubricant is selected from the group consisting of magnesium stearate, calcium stearate, or a combination thereof.

In the fifth aspect of the present invention, a use of the salt form according to the first aspect of the invention or the salt form combination according to the second aspect of the invention or the pharmaceutical composition of the fourth aspect of the invention is provided, for preparation of a medicament for preventing or treating type II diabetes mellitus and/or complications of type II diabetes mellitus.

In another preferred embodiment, the complications of type II diabetes mellitus are selected from the group consisting of coronary artery disease, stroke, hypertension, nephropathy, peripheral vascular disease, neurological disease, and retinopathy.

In the sixth aspect of the present invention, a method for treating or preventing type II diabetes mellitus and/or complications of type II diabetes mellitus is provided, and the method comprises the steps of administering to a patient a therapeutically effective amount of the hydrochloride, the maleate, the phosphate, the glycolate of the compound of formula I according to the first aspect of the invention or a combination thereof, or the salt form combination according to the second aspect of the invention, or the pharmaceutical composition according to the fourth aspect of the invention.

It should be understood that in the present invention, any of the technical features specifically described above and below (such as in the Examples) can be combined with each other, thereby constituting new or preferred technical solutions which will not redundantly be described one by one herein.

DETAILED DESCRIPTION OF INVENTION

Figure 1:
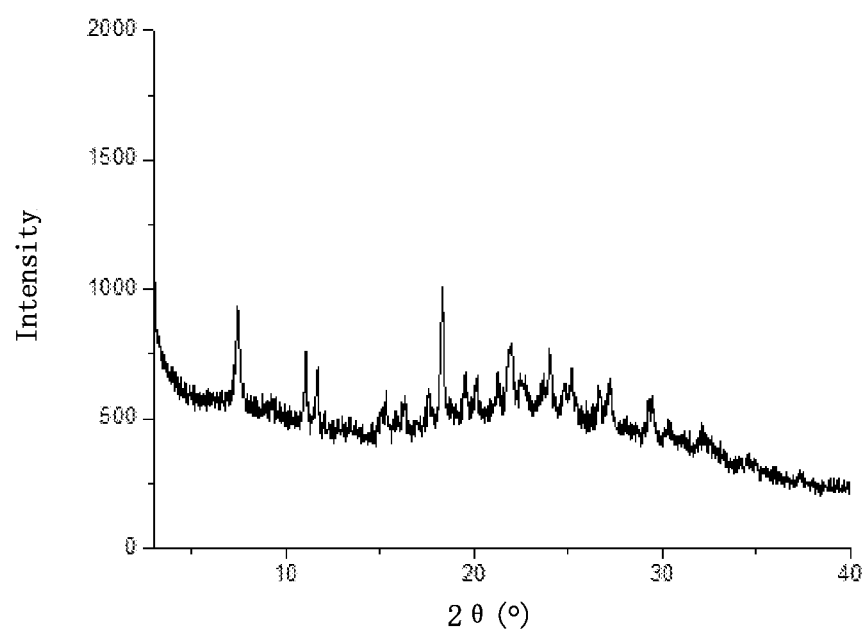
FIG. 1 is an XRD pattern of the hydrochloride of Example 1 of the present invention.

Through extensive and intensive research, the inventors have unexpectedly prepared a salt form of (R)-methyl-2-(3-aminopiperidin-1-yl)-3-(2-cyanobenzyl)-4-carbonyl-3,4-dihydrothiophene[3,2-d]pyrimidine-6-carboxylic acid with better pharmaceutical properties. Based on the above findings, the inventors have completed the present invention.

Compound of Formula I

The compound of formula I according to the invention is (R)-methyl-2-(3-aminopiperidin-1-yl)-3-(2-cyanobenzyl)-4-carbonyl-3,4-dihydrothiophene[3,2-d]pyrimidine-6-carboxylic acid.

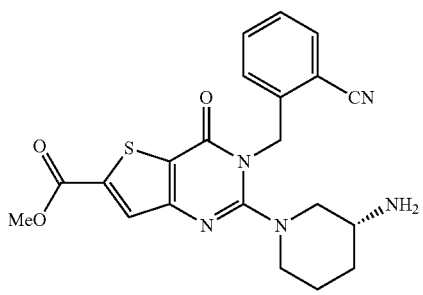

I (R)-methyl-2-(3-aminopiperidin-1-yl)-3-(2-cyanobenzyl)-4-carbonyl-3,4-dihy drothiophene[3,2-d]pyrimidine-6-carboxylic acid (Formula I) is a novel DPP IV selective, reversible competitive inhibitor with strong hypoglycemic activity in vivo. Its inhibitory activity is up to nanomolar level, and its DPP IV inhibitory activity and selectivity in vitro are superior to the marketed drugs, sitagliptin and vildagliptin.

In animals, the compound of formula I is effective in inhibiting DPP IV activity in normal mice and rat plasma, and its DPP IV inhibitory activity is superior to the marketed drug alogliptin. The compound of formula I can increase the oral glucose tolerance of normal ICR mice in a dose-dependent manner, and the onset dose is only 0.1 mg/kg, which is better than alogliptin; the compound can effectively decrease fasting blood glucose of ob/ob mice when it is chronic administered to ob/ob mice, which is superior to the positive control drug alogliptin; the chronic administration of the compound can reduce its fasting blood glucose of the gene-deficient db/db mice, which is comparable to the positive control drug alogliptin.

Pharmacokinetics and safety studies have shown that the compound of formula I has good pharmacokinetic properties and safety in rats and dogs, and its half-life and $AUC_{0-t}$ are superior to those of the marketed drug alogliptin in rats and dogs. The compound is safe and the acute toxicity test of ICR mice shows that no animal died in the 300 mg/kg administration group. The acute toxicity test of Beagle dogs shows that there is no animal death in the 1 g/kg administration group. The subacute toxicity experiment of rats shows that there is no obvious toxicity reaction in 150 mg/kg orally administrated group.

Based on the results of pharmacodynamic evaluation in vitro, pharmacological evaluation in vivo, pharmacokinetic study and safety evaluation etc., the hypoglycemic effect of this compound in vivo is superior to that of the currently clinically used DPPIV inhibitor.

Free Base of the Compound of Formula I

In the present invention, the free base of (R)-methyl-2-(3-aminopiperidin-1-yl)-3-(2-cyanobenzyl)4-carbonyl-3,4-dihydrothiophene[3,2-d]pyrimidine-6-carboxylic acid powder is obtained by the preparation method described in CN201210262331.3. $^1$H NMR (CDCl$_3$): δ 7.76 (s, 1H), 7.610 (d, 1H), 7.493 (t, 1H), 7.320 (t, 1H), 7.180 (d, 1H), 5.500 (quartet, 2H), 3.895 (s, 3H), 3.680 (d, 2H), 3.355 (m, 1H), 3.010 (m, 2H), 2.150 (m, 1H), 1.894 (m, 2H), 1.644 (m, 1H); LC-MS m/z 424.1 [M+H]$^+$.

Hydrochloride

The present invention provides a hydrochloride of a compound of formula I.

In another preferred embodiment, the hydrochloride is a crystal.

In another preferred embodiment, the X-ray powder diffraction pattern of the hydrochloride crystal includes 3 or more 2θ values selected from the group consisting of: 7.43±0.2°, 11.06±0.2°, 11.70±0.2°, 13.46±0.2°, 15.03±0.2°, 15.34±0.2°, 18.32±0.2°, 21.96±0.2°, 24.01±0.2°, 27.20±0.2°, 29.32±0.2°, 30.26±0.2°.

In another preferred embodiment, the X-ray powder diffraction pattern of the hydrochloride crystal includes 3 or more 2θ values selected from the group consisting of 7.43°, 11.06°, 11.70°, 18.32°, 21.96°, 24.01°, 27.20°, 29.32°, 30.26°.

In another preferred embodiment, the X-ray powder diffraction pattern of the hydrochloride crystal includes 3 or more 2θ values selected from the group consisting of: 7.43±0.2°, 11.06±0.2°, 11.70±0.2°, 13.46±0.2°, 15.03±0.2°, 15.34±0.2°, 15.84±0.2°, 16.35±0.2°, 17.59±0.2°, 18.32±0.2°, 19.54±0.2°, 20.13±0.2°, 21.24±0.2°, 21.96±0.2°, 22.46±0.2°, 22.74±0.2°, 23.67±0.2°, 24.01±0.2°, 24.83±0.2°, 25.19±0.2°, 26.63±0.2°, 27.20±0.2°, 29.32±0.2°, 30.26±0.2°, 32.15±0.2°.

In another preferred embodiment, the X-ray powder diffraction pattern of the hydrochloride crystal is substantially characterized as in FIG. 1.

In another preferred embodiment, the X-ray powder diffraction pattern of the hydrochloride crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the hydrochloride crystal, there is no melting peak prior to decomposition.

Figure 3:
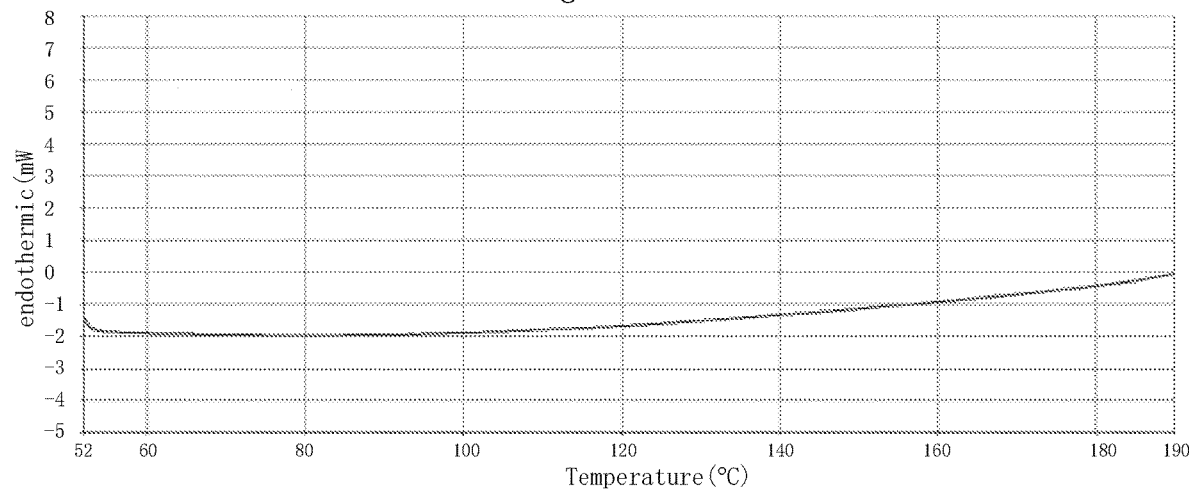
FIG. 3 is a differential scanning calorimetry (DSC) analysis spectrum of the hydrochloride of Example 1 of the present invention.

In another preferred embodiment, the DSC spectrum of the hydrochloride crystal is substantially as shown in FIG. 3.

In another preferred embodiment, in the TG pattern of the hydrochloride crystal, there is a characteristic absorption peak at 272±2° C.

In another preferred embodiment, in the TG pattern of the hydrochloride crystal, there is a characteristic absorption peak at 272.6° C.

Figure 2:
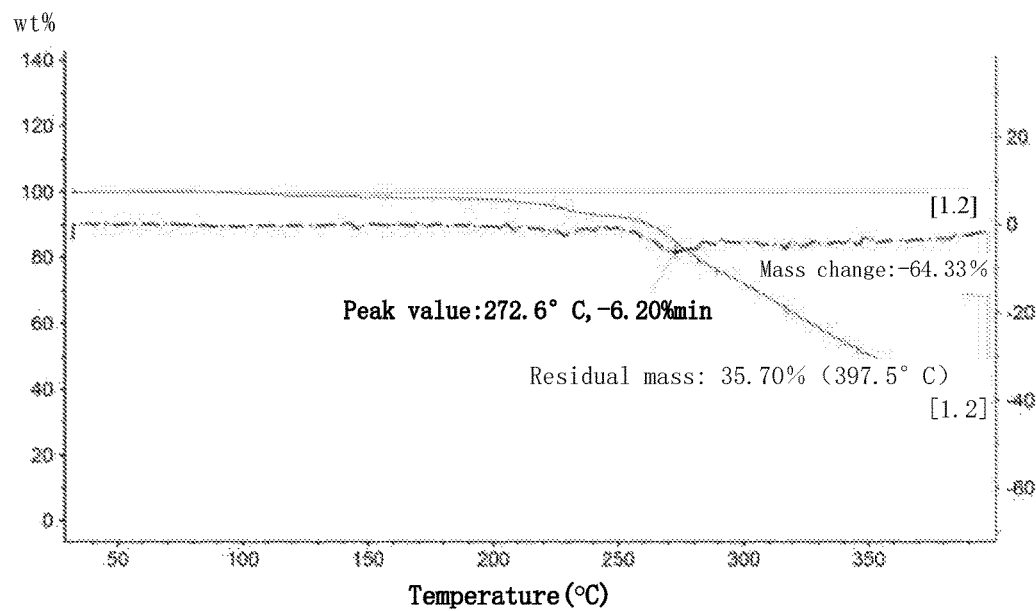
FIG. 2 is a TG diagram of the hydrochloride of Example 1 of the present invention.

In another preferred embodiment, the thermogravimetric analysis pattern (TG pattern) of the hydrochloride crystal is substantially characterized as in FIG. 2.

In another preferred embodiment, the thermal weight loss of the hydrochloride crystal is 64-65 wt % at 400° C., preferably 64.33 wt %.

In another preferred embodiment, the weight gain of the hydrochloride crystal is calculated to be ≤3%, preferably ≤1%, more preferably ≤0.3%, after being placed in a desiccator having a humidity of 50% for 24 hours and taken out.

Figure 4:
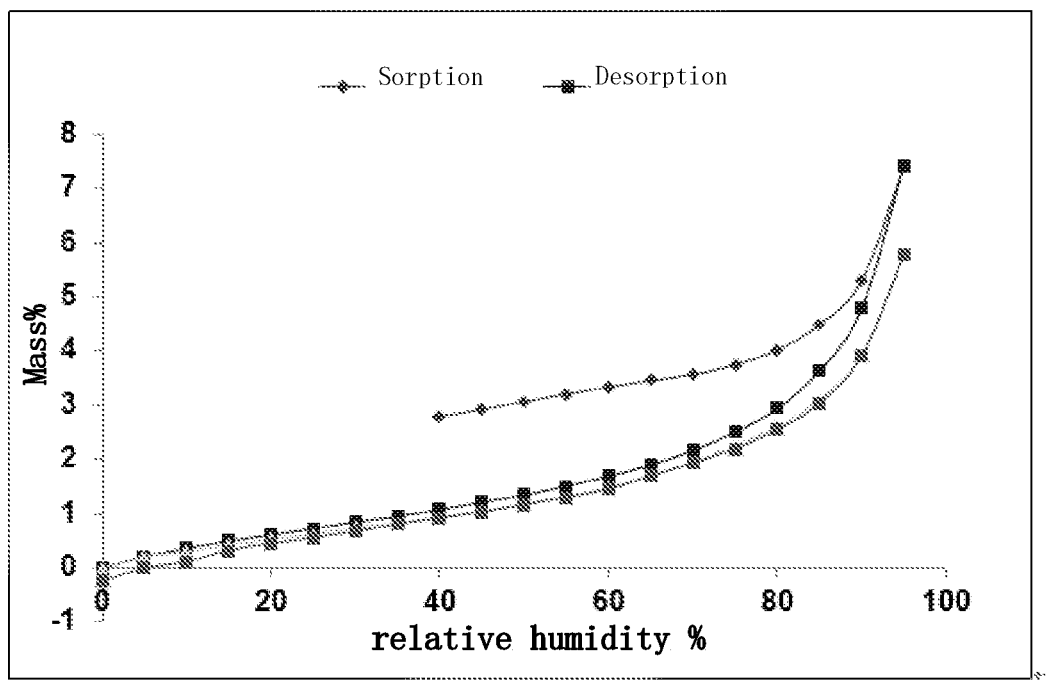
FIG. 4 is a hygroscopicity analysis (DVS) spectrum of the hydrochloride of Example 1 of the present invention.

In another preferred embodiment, the DVS pattern of the hydrochloride crystal is substantially as shown in FIG. 4.

In another preferred embodiment, the IR pattern of the hydrochloride crystal includes 3 or more characteristic absorption peaks represented by the wavelength λ selected from the group consisting of: $3429±2$ cm$^{-1}$, $2951±2$ cm$^{-1}$, $2827±2$ cm$^{-1}$, $2225±2$ cm$^{-1}$, $1720±2$ cm$^{-1}$, $1687±2$ cm$^{-1}$, $1560±2$ cm$^{-1}$, $1533±2$ cm$^{-1}$, $1446±2$ cm$^{-1}$, $1385±2$ cm$^{-1}$, $1261±2$ cm$^{-1}$, $1064±2$ cm$^{-1}$, $771±2$ cm$^{-1}$.

Figure 5:
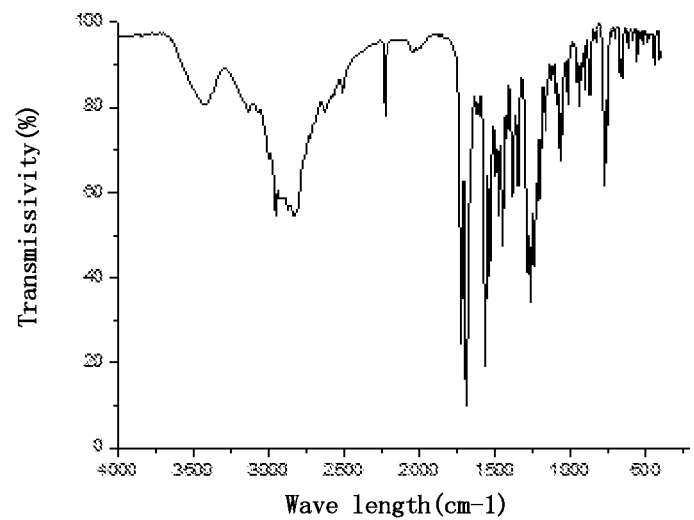
FIG. 5 is an infrared spectrum (IR) spectrum of the hydrochloride of Example 1 of the present invention.

In another preferred embodiment, the IR pattern of the hydrochloride crystal is substantially as shown in FIG. 5.

Figure 6:
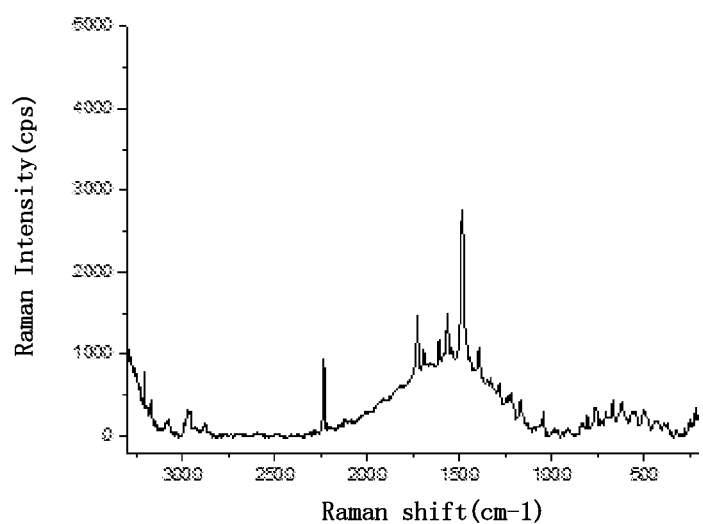
FIG. 6 is a Raman spectrum of the hydrochloride of Example 1 of the present invention.

In another preferred embodiment, the Raman diagram of hydrochloride crystal is substantially as shown in FIG. 6.

Maleate

The present invention provides a maleate of a compound of formula I.

In another preferred embodiment, the maleate is a crystal.

In another preferred embodiment, the X-ray powder diffraction pattern of the maleate crystal includes 3 or more 2θ values selected from the group consisting of 7.55±0.2°, 12.41±0.2°, 15.45±0.2°, 17.50±0.2°, 20.89±0.2°, 26.59±0.2°, 26.93±0.2°.

In another preferred embodiment, the X-ray powder diffraction pattern of the maleate crystal includes 3 or more 2θ values selected from the group consisting of 7.55±0.2°, 12.41±0.2°, 15.45±0.2°, 17.50±0.2°, 20.89±0.2°, 26.59±0.2°, 26.93±0.2°, 27.10±0.2°, 28.21±0.2°, 30.53±0.2°, 32.96±0.20.

In another preferred embodiment, the X-ray powder diffraction pattern of the maleate crystal includes 3 or more 2θ values selected from the group consisting of 7.55±0.2°, 10.83±0.2°, 12.41±0.2°, 13.22±0.2°, 14.38±0.2°, 14.75±0.2°, 15.45±0.2°, 15.80±0.2°, 17.50±0.2°, 18.30±0.2°, 19.40±0.2°, 20.43±0.2°, 20.89±0.2°, 21.85±0.2°, 22.87±0.2°, 23.25±0.2°, 25.04±0.2°, 26.59±0.2°, 26.93±0.2°, 27.10±0.2°, 28.21±0.2°, 30.53±0.2°, 32.96±0.2°.

Figure 7:
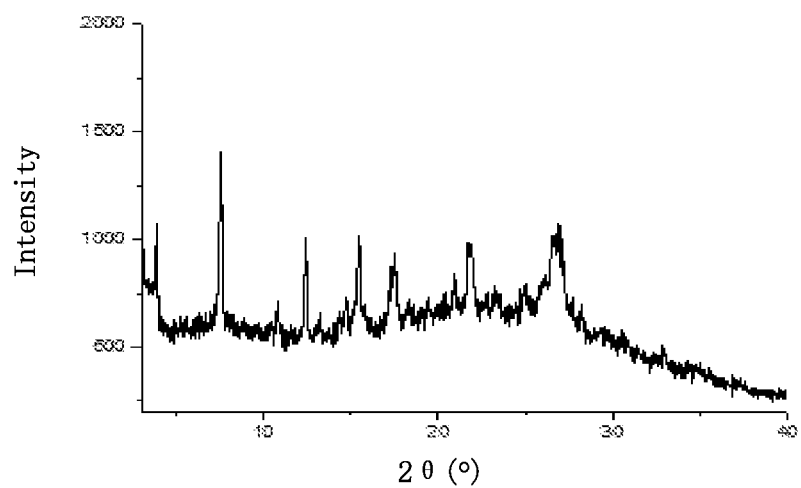
FIG. 7 is an XRD pattern of the maleate of Example 2 of the present invention.

In another preferred embodiment, the X-ray powder diffraction pattern of the maleate crystal is substantially characterized as in FIG. 7.

In another preferred embodiment, the X-ray powder diffraction pattern of the maleate crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the maleate crystal, there is a characteristic absorption peak at 113±5° C.

In another preferred embodiment, in the differential scanning calorimetry analysis spectrum (DSC spectrum) of the maleate crystal, there is a characteristic absorption peak at 113.8° C.

Figure 9:
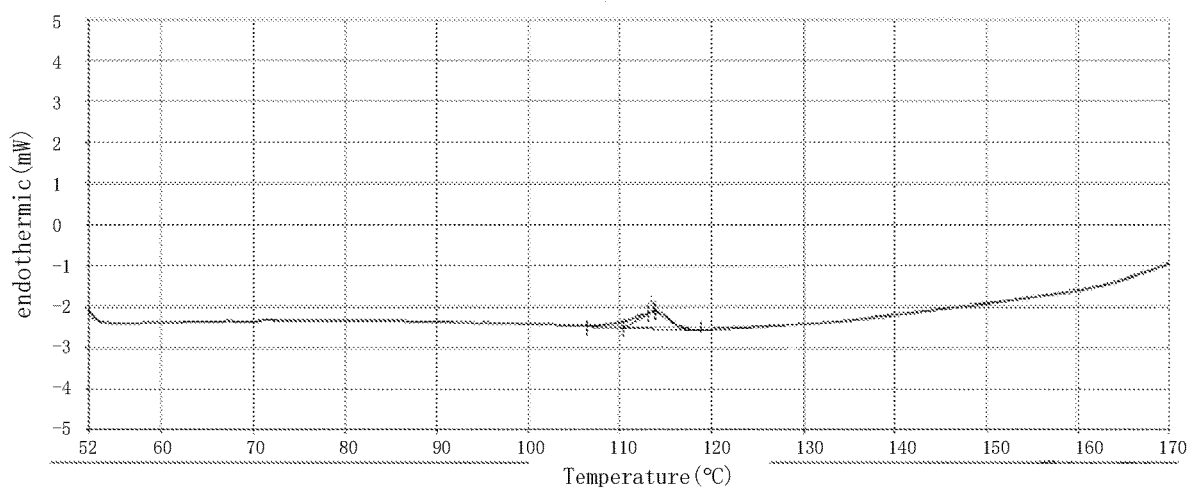
FIG. 9 is a differential scanning calorimetry (DSC) analysis spectrum of the maleate of Example 2 of the present invention.

In another preferred embodiment, the DSC pattern of the maleate crystal is substantially as shown in FIG. 9.

In another preferred embodiment, the TG pattern of the maleate crystal comprises a characteristic absorption peak selected from the group consisting of 77±2° C., 180±5° C. and 284±5° C.

In another preferred embodiment, the TG pattern of the maleate crystal comprises a characteristic absorption peak selected from the group consisting of 77.3° C., 179.6° C. and 283.6° C.

Figure 8:
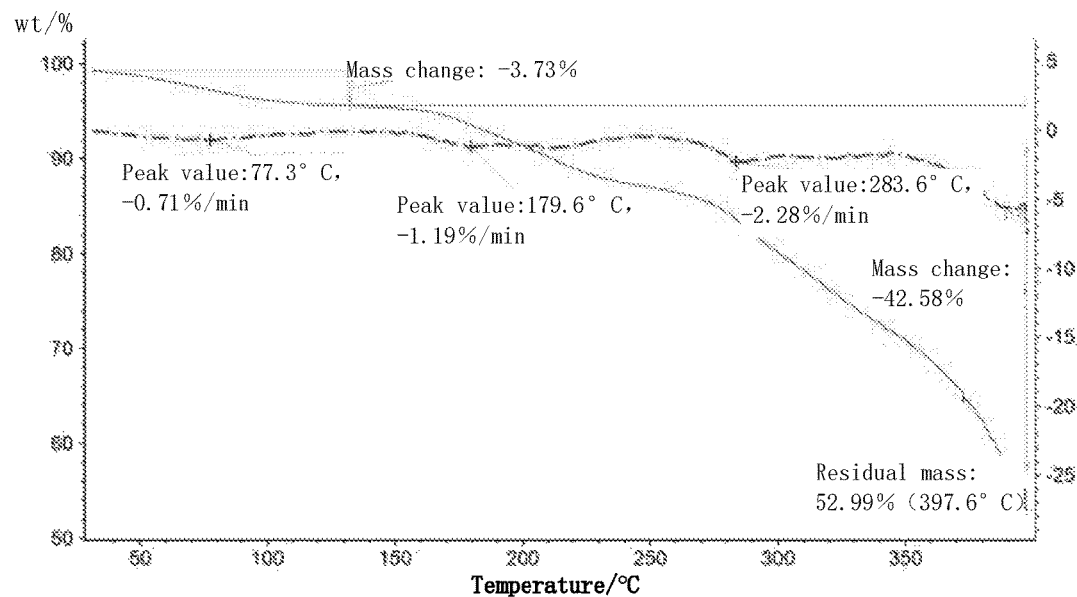
FIG. 8 is a TG diagram of the maleate of Example 2 of the present invention.

In another preferred embodiment, the thermogravimetric analysis pattern (TG pattern) of the maleate crystal is substantially characterized as in FIG. 8.

In another preferred embodiment, the thermal weight loss of the maleate crystal is 42-43 wt % at 400° C., preferably 42.58 wt %.

In another preferred embodiment, the starting value of the endothermic transition temperature of the maleate crystal is 110±2° C., preferably 110.37° C.

In another preferred embodiment, the weight gain of the maleate crystal is calculated to be ≤3%, preferably ≤1%, more preferably ≤0.3%, after being placed in a desiccator having a humidity of 50% for 24 hours and taken out.

Figure 10:
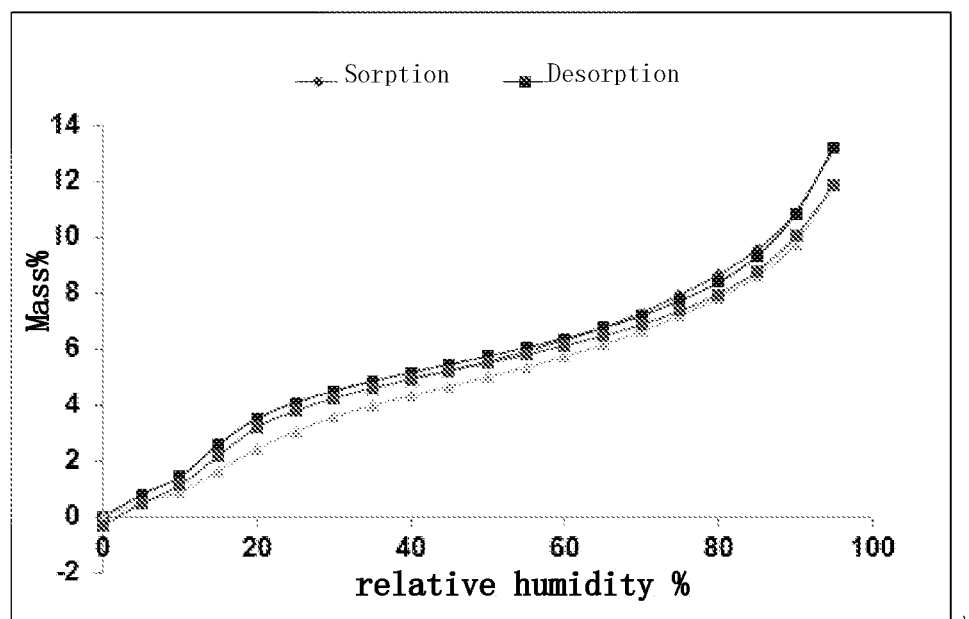
FIG. 10 is a hygroscopicity analysis (DVS) spectrum of the maleate of Example 2 of the present invention.

In another preferred embodiment, the DVS pattern of the maleate crystal is substantially as shown in FIG. 10.

In another preferred embodiment, the IR pattern of the maleate comprises 3 or more characteristic absorption peaks represented by the wavelength λ selected from the group consisting of: $3429±2$ cm$^{-1}$, $3062±2$ cm$^{-1}$, $2954±2$ cm$^{-1}$, $2862±2$ cm$^{-1}$, $2224±2$ cm$^{-1}$, $1720±2$ cm$^{-1}$, $1676±2$ cm$^{-1}$, $1558±2$ cm$^{-1}$, $1531±2$ cm$^{-1}$, $1469±2$ cm$^{-1}$, $1354±2$ cm$^{-1}$, $1290±2$ cm$^{-1}$, $1219±2$ cm$^{-1}$, $1063±2$ cm$^{-1}$, $864±2$ cm$^{-1}$, $775±2$ cm$^{-1}$, $654±2$ cm$^{-1}$.

Figure 11:
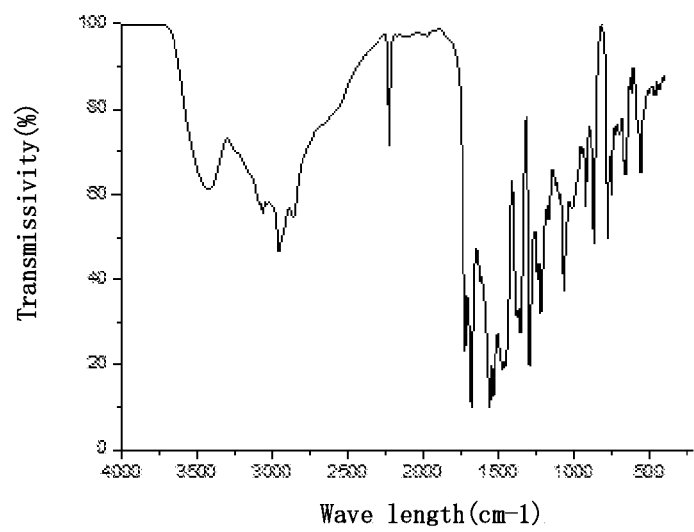
FIG. 11 is an infrared (IR) spectrum of the maleate of Example 2 of the present invention.

In another preferred embodiment, the IR pattern of the maleate crystal is substantially as shown in FIG. 11.

Figure 12:
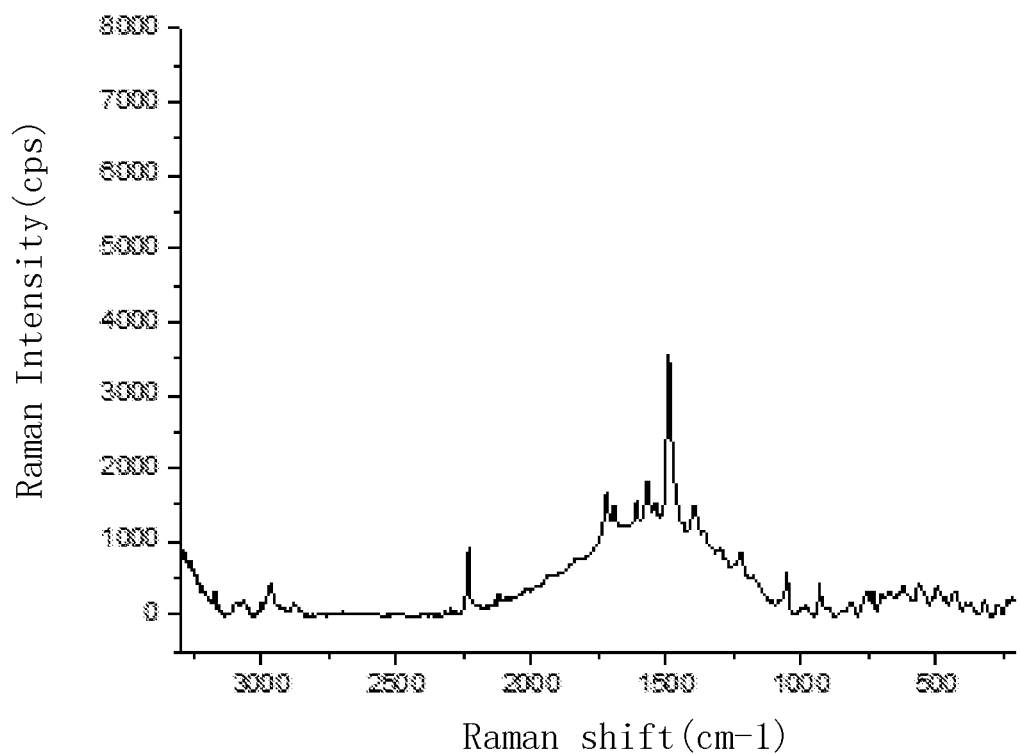
FIG. 12 is a Raman spectrum of the maleate of Example 2 of the present invention.

In another preferred embodiment, the Raman diagram of the maleate crystal is substantially as shown in FIG. 12.

Phosphate

The present invention provides a phosphate of a compound of formula I.

In another preferred embodiment, the phosphate is a crystal.

In another preferred embodiment, the X-ray powder diffraction pattern of the phosphate crystal comprises 3 or more 2θ values selected from the group consisting of 11.99±0.2°, 12.20±0.2°, 14.80±0.2°, 20.11±0.2°, 20.46±0.2°, 24.18±0.2°, 24.68±0.2°.

In another preferred embodiment, the X-ray powder diffraction pattern of the phosphate crystal comprises 3 or more 2θ values selected from the group consisting of 11.99±0.2°, 12.20±0.2°, 14.80±0.2°, 20.11±0.2°, 20.46±0.2°, 23.15±0.2°, 24.18±0.2°, 24.68±0.2°, 25.63±0.2°, 26.15±0.2°.

In another preferred embodiment, the X-ray powder diffraction pattern of the phosphate crystal comprises 3 or more 2θ values selected from the group consisting of 6.23±0.2°, 11.99±0.2°, 12.20±0.2°, 14.80±0.2°, 15.16±0.2°, 16.04±0.2°, 16.56±0.2°, 17.90±0.2°, 20.11±0.2°, 20.46±0.2°, 22.74±0.2°, 23.15±0.2°, 24.18±0.2°, 24.68±0.2°, 25.63±0.2°, 26.15±0.2°.

Figure 13:
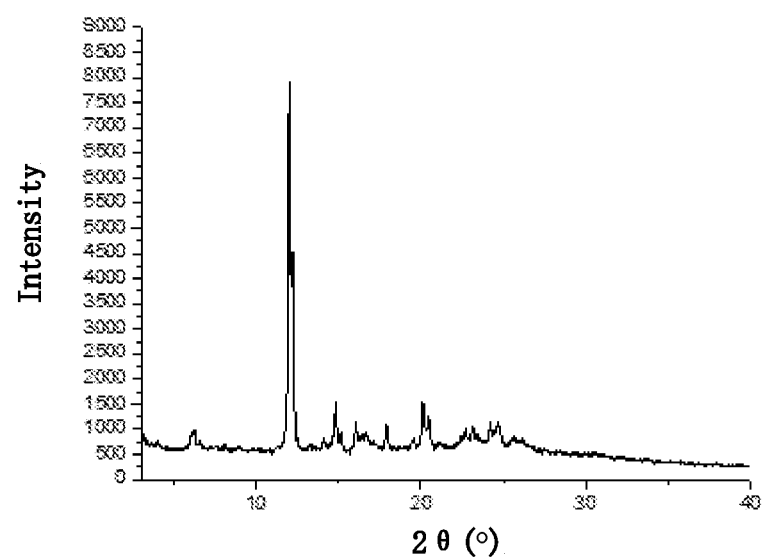
FIG. 13 is an XRD pattern of the phosphate of Example 3 of the present invention.

In another preferred embodiment, the X-ray powder diffraction pattern of the phosphate crystal is substantially characterized as in FIG. 13.

In another preferred embodiment, the X-ray powder diffraction pattern of the phosphate crystal has a deviation of ±0.5° from a characteristic absorption peak represented by a 2θ value, preferably a deviation of ±0.3°, more preferably a deviation of ±0.1°.

In another preferred embodiment, in the differential scanning calorimetry analysis spectrum (DSC spectrum) of the phosphate crystal, there is a characteristic absorption peak at 155±5° C., preferably 154.8° C.

Figure 15:
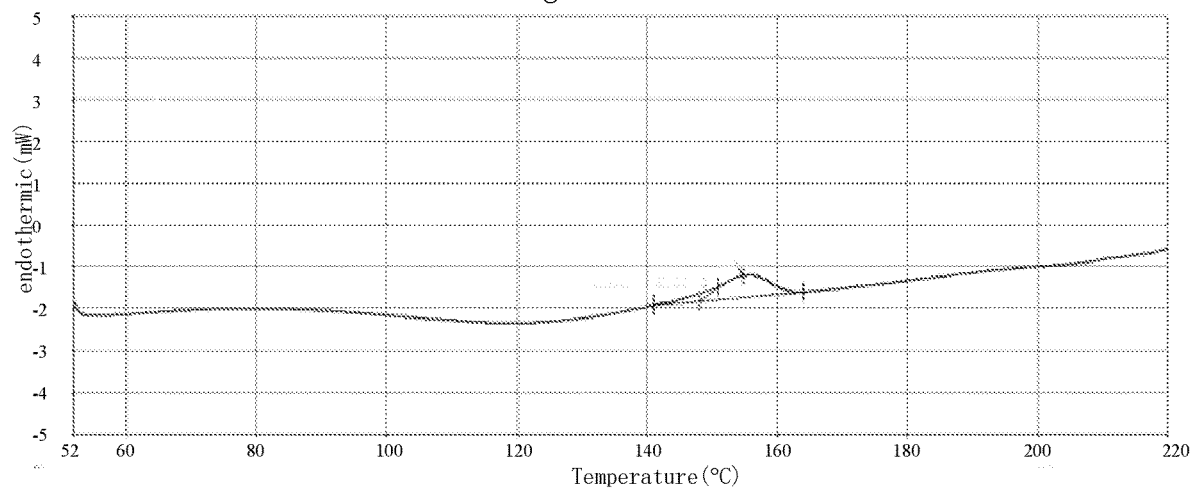
FIG. 15 is a differential scanning calorimetry (DSC) analysis spectrum of the phosphate of Example 3 of the present invention.

In another preferred embodiment, the DSC pattern of the phosphate crystal is substantially as shown in FIG. 15.

In another preferred embodiment, in the TG pattern of the phosphate crystal, there is a characteristic absorption peak at 361±2° C., preferably 361.0° C.

In another preferred embodiment, the thermal weight loss of the phosphate crystal is 47-48 wt % at 400° C., preferably 47.57 wt %.

Figure 14:
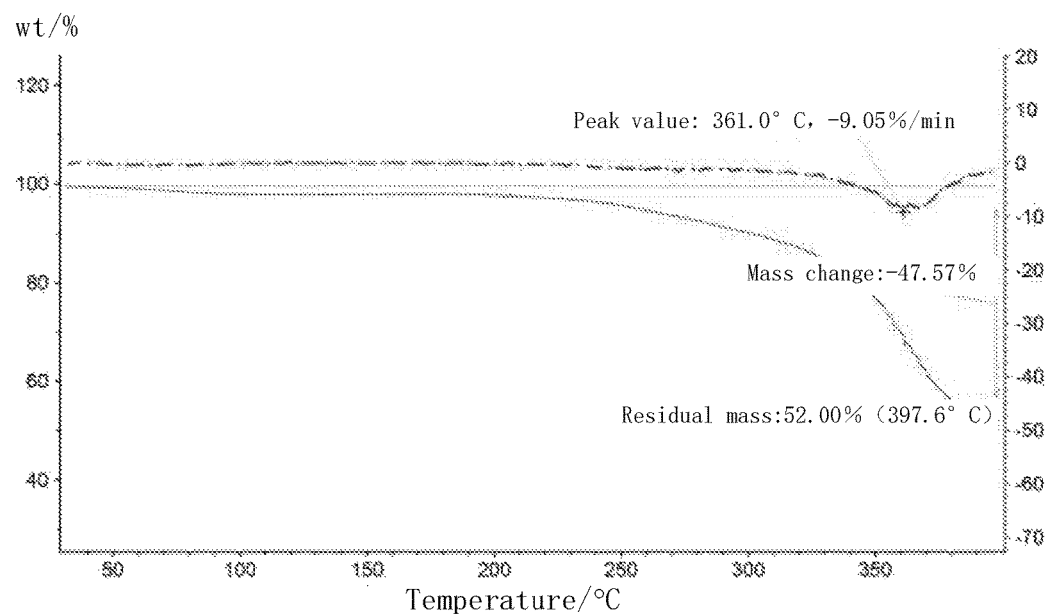
FIG. 14 is a TG diagram of the phosphate of Example 3 of the present invention.

In another preferred embodiment, the thermogravimetric analysis pattern (TG pattern) of the phosphate crystal is substantially characterized as in FIG. 14.

In another preferred embodiment, the starting value of the endothermic transition temperature of the phosphate crystal is 148±2° C., preferably 148.0° C.

In another preferred embodiment, the weight gain of the phosphate crystal is calculated to be ≤3%, preferably ≤1%, more preferably ≤0.3%, after being placed in a desiccator having a humidity of 50% for 24 hours and taken out.

Figure 16:
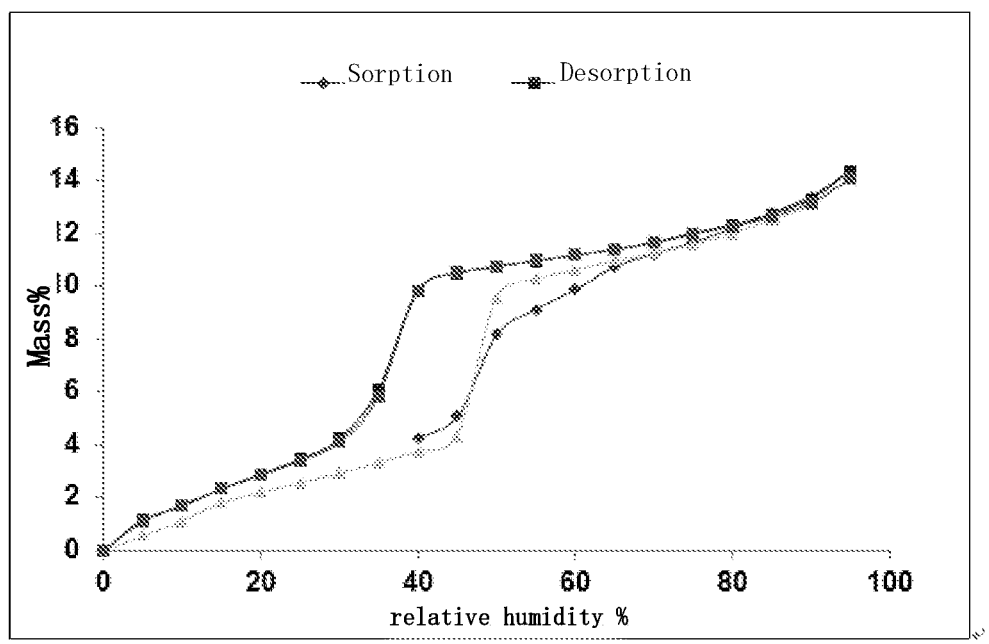
FIG. 16 is a hygroscopicity analysis (DVS) spectrum of the phosphate of Example 3 of the present invention.

In another preferred embodiment, the DVS pattern of phosphate crystal is substantially as shown in FIG. 16.

In another preferred embodiment, the IR pattern of the phosphate crystal comprises 3 or more characteristic absorption peaks represented by the wavelength λ selected from the group consisting of: $3408±2$ $cm^{-1}$, $2951±2$ $cm^{-1}$, $2860±2$ $cm^{-1}$, $2225±2$ $cm^{-1}$, $1716±2$ $cm^{-1}$, $1684±2$ $cm^{-1}$, $1601±2$ $cm^{-1}$, $1556±2$ $cm^{-1}$, $1531±2$ $cm^{-1}$, $1450±2$ $cm^{-1}$, $1379±2$ $cm^{-1}$, $1282±2$ $cm^{-1}$, $1238±2$ $cm^{-1}$, $1124±2$ $cm^{-1}$, $1064±2$ $cm^{-1}$, $947±2$ $cm^{-1}$, $868±2$ $cm^{-1}$, $758±2$ $cm^{-1}$, $521±2$ $cm^{-1}$.

Figure 17:
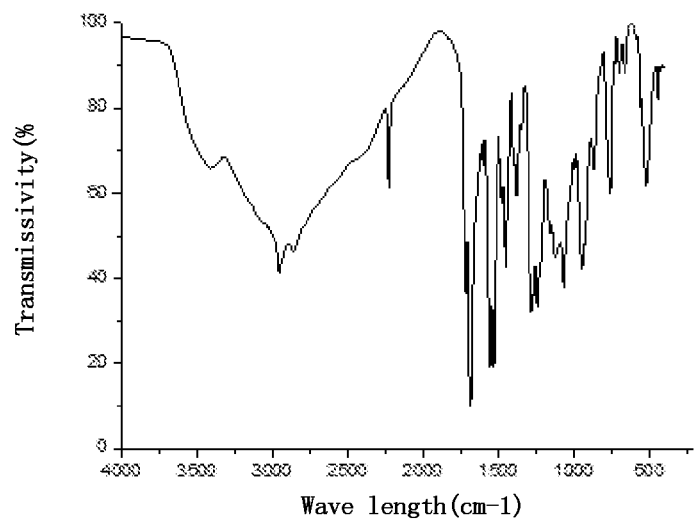
FIG. 17 is an infrared (IR) spectrum of the phosphate of Example 3 of the present invention.

In another preferred embodiment, the IR pattern of phosphate crystal is substantially as shown in FIG. 17.

Figure 18:
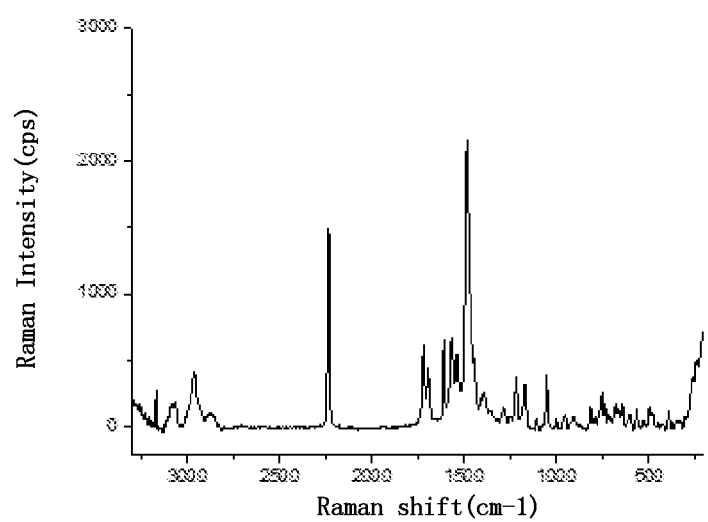
FIG. 18 is a Raman spectrum of the phosphate of Example 3 of the present invention.

In another preferred embodiment, the Raman diagram of the phosphate crystal is substantially as shown in FIG. 18.

Glycolate

The present invention provides a glycolate of a compound of formula I,

In another preferred embodiment, the glycolate is a crystal.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°, 20.51±0.2°, 21.22±0.2°, 21.78±0.2°, 23.00±0.2°.

In another preferred embodiment, the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°, 20.51±0.2°, 21.22±0.2°, 21.78±0.2°, 23.00±0.2°, 23.87±0.2°, 24.08±0.2°, 24.37±0.2°, 25.52±0.2°, 33.81±0.2°.

In another preferred embodiment, the X-ray powder diffraction pattern of the glycolate crystal includes 3 or more 2θ values selected from the group consisting of 6.66±0.2°, 8.92±0.2°, 9.91±0.2°, 10.20±0.2°, 13.35±0.2°, 13.92±0.2°, 15.78±0.2°, 16.71±0.2°, 16.89±0.2°, 17.41±0.2°, 18.70±0.2°, 19.37±0.2°, 20.12±0.2°, 20.51±0.2°, 21.22±0.2°, 21.78±0.2°, 22.75±0.2°, 23.00±0.2°, 23.87±0.2°, 24.08±0.2°, 24.37±0.2°, 25.52±0.2°, 26.44±0.2°, 27.02±0.2°, 27.48±0.2°, 28.23±0.2°, 28.63±0.2°, 28.84±0.2°, 29.68±0.2°, 30.14±0.2°, 30.51±0.2°, 31.41±0.2°, 31.76±0.2°, 33.00±0.2°, 33.81±0.2°, 34.13±0.2°, 35.21±0.2°, 25.83±0.2°, 36.37±0.2°, 37.70±0.2°, 37.93±0.2°.

Figure 19:
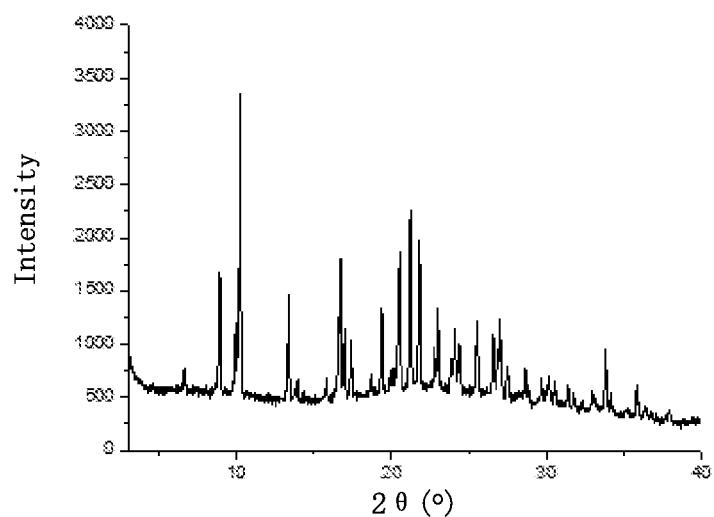
FIG. 19 is an XRD pattern of the glycolate of Example 4 of the present invention.

In another preferred embodiment, the X-ray powder diffraction pattern of the glycolate crystal is substantially characterized as in FIG. 19.

In another preferred embodiment, the X-ray powder diffraction pattern of the glycolate crystal has a deviation of ±0.5° from the characteristic absorption peak represented by the 2θ value, preferably a deviation of ±0.3°, more preferably a deviation of ±0.1°.

In another preferred embodiment, the differential scanning calorimetry analysis spectrum (DSC spectrum) of the glycolate crystal has a characteristic absorption peak at 189±5° C.

Figure 21:
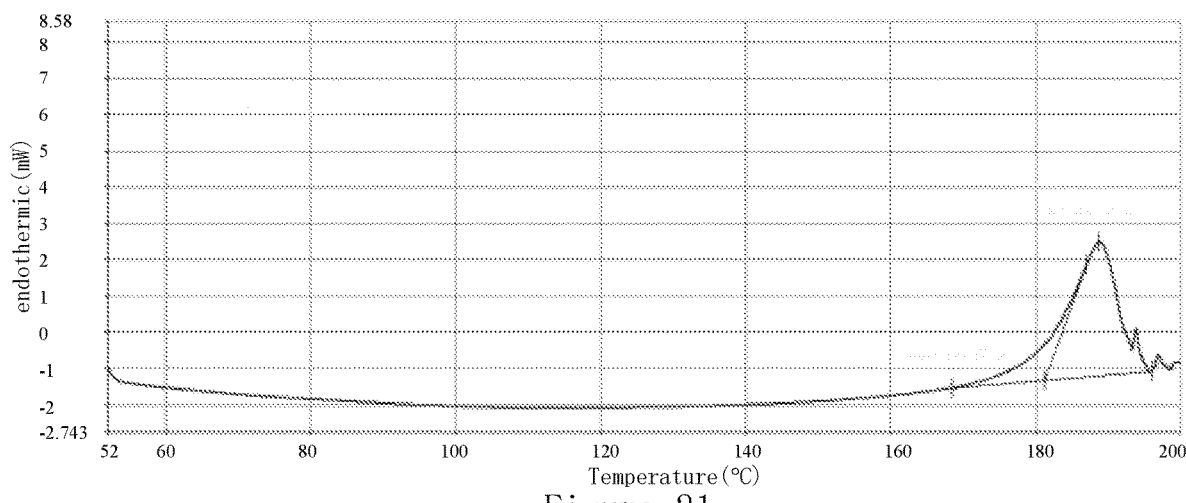
FIG. 21 is a differential scanning calorimetry (DSC) analysis spectrum of the glycolate of Example 4 of the present invention.

In another preferred embodiment, the DSC pattern of glycolate crystal is substantially as shown in FIG. 21.

In another preferred embodiment, the starting value of the endothermic transition temperature of the glycolate crystal is 148±2° C., preferably 148.0° C.

In another preferred embodiment, in the TG pattern of the glycolate crystal, there is a characteristic absorption peak at 192±2° C. and 268±2° C., preferably 192.5° C., 268.0° C.

Figure 20:
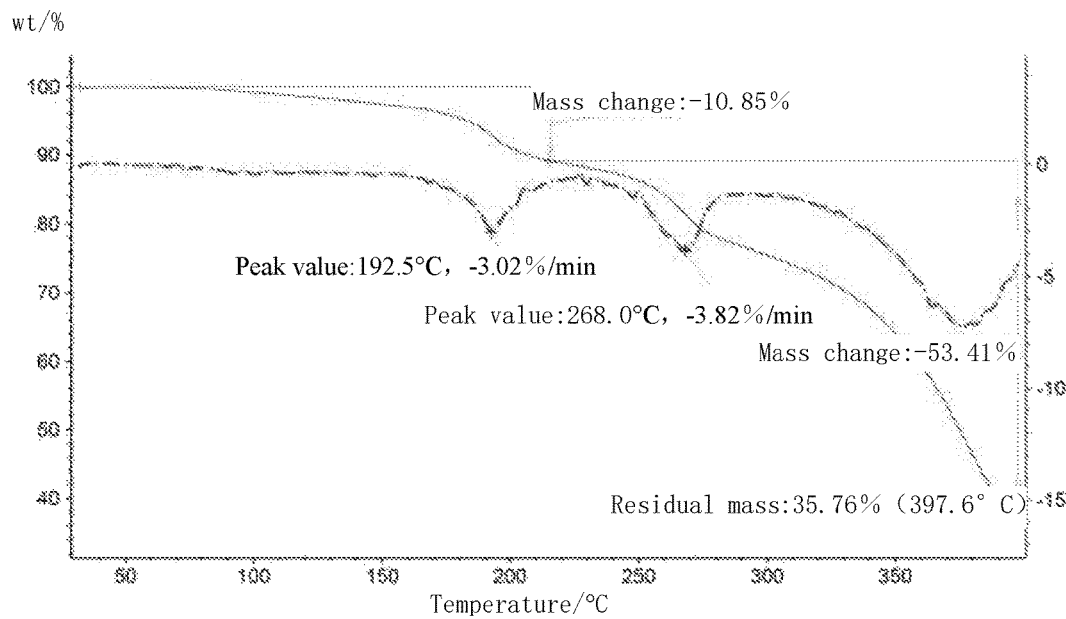
FIG. 20 is a TG diagram of the glycolate of Example 4 of the present invention.

In another preferred embodiment, the TG pattern of the glycolate crystal is substantially as shown in FIG. 20.

In another preferred embodiment, the thermal weight loss of the glycolate crystal is 53-54 wt % at 400° C., preferably 53.41 wt %.

In another preferred embodiment, the weight gain of the glycolate crystal is calculated to be ≤3%, preferably ≤1%, more preferably ≤0.3%, after being placed in a desiccator having a humidity of 50% for 24 hours and taken out.

Figure 22:
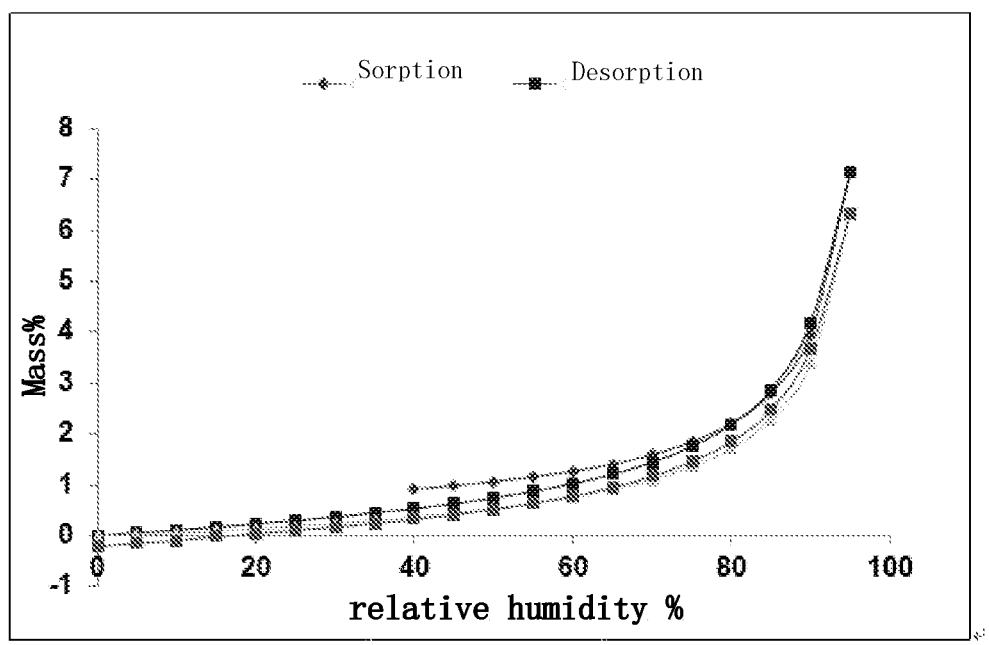
FIG. 22 is a hygroscopicity analysis (DVS) spectrum of the glycolate of Example 4 of the present invention.

In another preferred embodiment, the DVS pattern of the glycolate crystal is substantially as shown in FIG. 22.

In another preferred embodiment, the IR pattern of the glycolate crystal includes 3 or more characteristic absorption peaks represented by the wavelength λ selected from the group consisting of $3462±2$ $cm^{-1}$, $2958±2$ $cm^{-1}$, $2837±2$ $cm^{-1}$, $2227±2$ $cm^{-1}$, $1720±2$ $cm^{-1}$, $1674±2$ $cm^{-1}$, $1558±2$ $cm^{-1}$, $1533±2$ $cm^{-1}$, $1450±2$ $cm^{-1}$, $1350±2$ $cm^{-1}$, $1282±2$ $cm^{-1}$, $1223±2$ $cm^{-1}$, $1072±2$ $cm^{-1}$, $928±2$ $cm^{-1}$, $760±2$ $cm^{-1}$, $692±2$ $cm^{-1}$.

Figure 23:
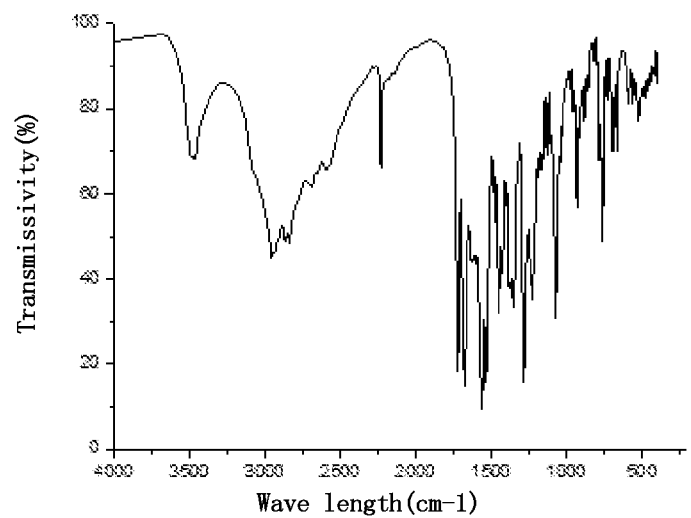
FIG. 23 is an infrared (IR) spectrum of the glycolate of Example 4 of the present invention.

In another preferred embodiment, the IR pattern of the glycolate is substantially as shown in FIG. 23.

Figure 24:
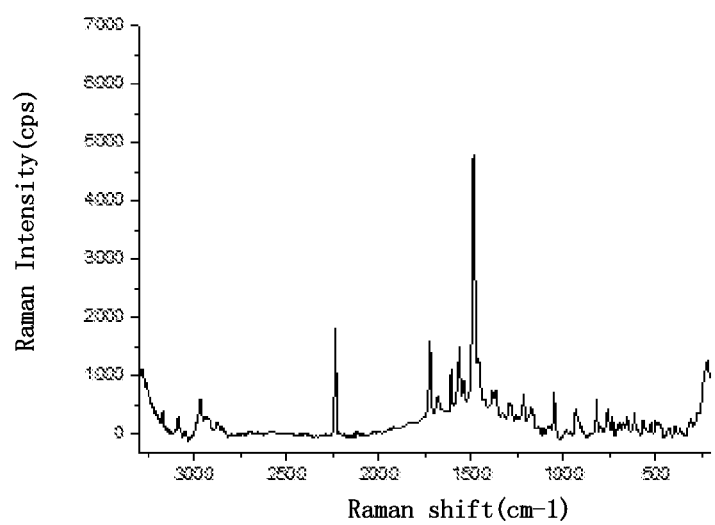
FIG. 24 is a Raman spectrum of the glycolate of Example 4 of the present invention.

In another preferred embodiment, the Raman diagram of the glycolate is substantially as shown in FIG. 24.

Salt Form Combination

In the present invention, the crystal composition comprises the hydrochloride, maleate, phosphate, glycolate or consists of the hydrochloride, maleate, phosphate, glycolate.

In another preferred embodiment, by the total weight of the crystal composition, the weight percentage of the hydrochloride, the maleate, the phosphate, the glycolate is 60-99.999%, preferably from 80-99.999%, more preferably 90-99.999%.

In another preferred embodiment, the crystal composition further comprises: hydrochloride, maleate, phosphate, glycolate of (R)-methyl-2-(3-aminopiperidin-1-yl)-3-(2-cyanobenzyl)-4-carbonyl-3,4-dihydrothiophene[3,2-d]pyrimidine-6-carboxylic acid, free base of (R)-methyl-2-(3-aminopiperidin-1-yl)-3-(2-cyanobenzyl)-4-carbonyl-3,4-dihydrothiophene [3,2-d]pyrimidine-6-carboxylic acid.

Preparation Method of Salt Form Compound

In the present invention, a method for the preparation of a salt form of the compound of formula I is provided, and the method comprises the following steps of:

(1) a free base of the compound of formula I is dissolved in a solvent and a certain amount of acid is added;

(2) the solution obtained in step (1) is allowed to be placed for a certain period of time to carry out a reaction at a certain temperature, and the crystal is crystallized with stirring to obtain solids;

(3) the solids obtained in step (2) are filtered and/or dried to obtain the salt form of the first aspect of the invention.

In another preferred embodiment, in step (1), the solvent is selected from the group consisting of a alcohol, ether, ketone, ester, or a combination thereof.

In another preferred embodiment, the alcohol is a C1-C10 alcohol, preferably C1-C8 alcohol, more preferably C1-C5 alcohol.

In another preferred embodiment, the alcohol is selected from the group consisting of a methanol, ethanol, n-propanol, isopropanol, n-butanol, neopentyl alcohol, or a combination thereof.

In another preferred embodiment, the ether is a C2-C8 ether, preferably a C2-C5 ether.

In another preferred embodiment, the ether is selected from the group consisting of ethyl ether, tetrahydrofuran, or a combination thereof.

In another preferred embodiment, the ester is a C1-C10 ester, preferably C1-C7 ester, more preferably C1-C5 ester.

In another preferred embodiment, the ester is selected from the group consisting of methyl formate, ethyl acetate, isobutyl formate, or a combination thereof.

In another preferred embodiment, in step (1), the molar ratio of the free base to the acid is 1:0.8-1:1.5, preferably 1:0.9-1:1.3, more preferably 1:1.0-1:1.1.

In another preferred embodiment, in step (1), the temperature ranges from 10 to 80° C., preferably from 30 to 50° C.

In another preferred embodiment, in step (1), the reaction time is from 0.1 to 10 h, preferably from 0.5 to 6 h.

In another preferred embodiment, in step (2), the drying temperature is from 10 to 90° C., preferably from 20 to 80° C., more preferably from 40 to 70° C.

In another preferred embodiment, in step (2), the drying pressure is 0 to 20 KPa, preferably 0 to 10 KPa, more preferably 5 to 10 KPa.

In another preferred embodiment, in step (2), the drying time is from 5 to 150 hours, preferably from 30 to 100 hours, more preferably from 60 to 80 hours.

In another preferred embodiment, in step (2), the crystallization is carried out at 0 to 50° C., preferably 0 to 40° C., more preferably 20 to 30° C.

In another preferred embodiment, the crystallization is carried out with stirring.

In another preferred embodiment, in step (3), the yield of the method is from 50% to 99.9%, preferably from 75% to 99.9%, more preferably from 85% to 99.9%.

Pharmaceutical Composition

The present invention provides a pharmaceutical composition comprising (1) the hydrochloride, the maleate, the phosphate, the glycolate of the compound of formula I according to the first aspect of the invention, or combinations thereof;

(2) a pharmaceutically acceptable excipient.

It should be understood that, in the present invention, the excipients are not particularly limited, which can be selected from conventional materials in the art, or may be prepared by conventional methods, or are commercially available.

Typically, the excipients include, but are not limited to, fillers, disintegrants, binders, lubricants, or combinations thereof.

Typically, the fillers include, but are not limited to, starch, lactose, microcrystalline cellulose, dextrin, mannitol, magnesium oxide, calcium sulfate, or combinations thereof.

Typically, the disintegrants include, but are not limited to, carboxymethylcellulose and salts thereof, croscarmellose and salts thereof, crospovidone, sodium carboxymethyl starch, low substituting hydroxypropyl cellulose, or combinations thereof.

Typically, the binders include, but are not limited to, povidone, hydroxypropyl methylcellulose, starch slurry, or combinations thereof.

Typically, the lubricants include, but are not limited to, magnesium stearate, calcium stearate, or combinations thereof.

Use

The present invention also provides a use of the hydrochloride, maleate, phosphate and glycolate of (R)-methyl-2-(3-aminopiperidin-1-yl)-3-(2-cyanobenzyl)-4-carbonyl-3,4-dihydrothiophene[3,2-d]pyrimidine-6-carboxylic acid or the salt form composition or the pharmaceutical composition, for preparation of a medicament for preventing or treating type II diabetes mellitus and/or complications of type II diabetes mellitus.

Typically, the complications of type II diabetes include, but are not limited to, coronary artery disease, stroke, hypertension, kidney disease, peripheral vascular disease, neurological disease, retinopathy.

The invention also provides a method for treating or preventing type II diabetes mellitus and/or complications of type II diabetes mellitus, including administering to a patient a therapeutically effective amount of the hydrochloride, maleate, phosphate and glycolate of (R)-methyl-2-(3-aminopiperidin-1-yl)-3-(2-cyanobenzyl)-4-carbonyl-3,4-dihydrothiophene[3,2-d]pyrimidine-6-carboxylic acid crystal or the salt form composition or the pharmaceutical composition.

The administration amount of the hydrochloride, maleate, phosphate and glycolate of the present invention or the pharmaceutical composition thereof varies depending on the age, sex, race, condition and the like of the patient.

The compound of the present invention may be administered alone or in combination with other drugs or active ingredients.

In the present invention, the administration mode of the crystalline form or the pharmaceutical composition of the present invention is not particularly limited. Administration modes identical or similar to conventional administration modes for (R)-methyl-2-(3-aminopiperidin-1-yl)-3-(2-cyanobenzyl)-4-carbonyl-3,4-dihydrothiophene[3,2-d] pyrimidine-6-carboxylic acid can be used, which includes (but not limited to) oral, transdermal, intravenous, intramuscular, topical route and the like.

The Invention has the Following Main Advantages:

(1) The hydrochloride, maleate, phosphate and glycolate of the present invention have higher purity;

(2) The hydrochloride, maleate, phosphate and glycolate of the present invention have superior stability, especially stability in water, enhanced oral absorption capacity and improved bioavailability;

(3) The hydrochloride, maleate, phosphate and glycolate crystalline forms of the present invention have lower hygroscopicity, and when the relative humidity is less than 50%, the hydrochloride, maleate, phosphate and glycolate have a hygroscopicity of ≤0.3%;

(4) The hydrochloride, maleate, phosphate and glycolate of the present invention are not easily degraded under conventional conditions;

(5) The preparation method of the hydrochloride, maleate, phosphate and glycolate of the invention is simple in operation, easy to control, of good reproducibility, and suitable for industrial production;

(6) The salt form compound of the present invention has superior oral hypoglycemic activity in preventing or treating type II diabetes.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

Unless otherwise defined, all professional and scientific terminology used in the text have the same meanings as known to the skilled in the art. In addition, any methods and materials similar or equal with the record content can apply to the methods of the invention. The method of the preferred embodiment described herein and the material are only for demonstration purposes.

Common Test Methods and Test Parameters

In the present invention, the crystal is subjected to a series of general tests as follows:

X-ray Diffraction (XRD) is a structural analysis method for spatial distribution of the inner atoms of a substance by X-ray diffraction formed by the crystal. When X-rays having a certain wavelength are irradiated onto a crystalline substance, the X-rays are scattered due to the presence of a regularly arranged atom or ion in the crystal, and the scattered X-rays are intensified in some directions to show unique diffraction phenomenon corresponding to crystalline structure.

In the present invention, the test parameters of XRD are as follows: instrument model: Bruker D8advance; target: Cu—$K_\alpha$ (40 kV, 40 mA); distance from sample to detector: 30 cm; scanning range: 3°~40° (2 theta value); scanning step: 0.1 s.

Thermo Gravimetric Analysis (TGA) is an analytical technique for determining the mass change of a substance with temperature under programmed temperature control conditions. Thermo Gravimetric Analysis can be used to obtain the heat generated by the thermal changes of the sample. It is suitable for checking the loss of crystallization solvent or crystal water molecules or the sublimation and decomposition process and value of the sample in a crystalline material. It can also effectively distinguish whether the material contains the crystallization solvent or crystalline water.

In the present invention, the test parameters of the TGA are as follows: Instrument type: Netzsch TG 209F3; Crucible: Alumina crucible; Temperature range: 30 to 400° C.; Scanning rate: 10 K/min; purge gas: 25 mL/min; Protective gas: 15 mL/min.

Differential Scanning Calorimeter (DSC) is a technique for determining the change of temperature difference between the sample and the inert reference (commonly used $\alpha$-$Al_2O_3$) with temperature by using programme controlling heating or cooling. DSC analysis is suitable for analysing the melt decomposition state, mixed crystal matter state, crystal transformation matter state etc. of the sample.

In the present invention, the test parameters of the DSC are as follows:

Instrument type: Perkin Elmer DSC 8500; Crucible: Aluminum crucible; Scanning from 50° C. to 280° C. at a heating rate of 10° C./min under nitrogen purge.

Dynamic vapor absorption (DVS) test/water absorption test rapidly measures the increase and loss of the moisture in the sample caused by flow carrier gas with set relative humidity (RH), wherein the sample is placed on a digital microbalance with high sensitivity and high stability at a self-suspension state, and then the adsorption/desorption of water vapor is measured by measuring the increase/decrease of mass of the material, thereby determining the hygroscopicity of the sample.

In the present invention, the test parameters of the DVS are as follows: Instrument type: SMS DVS Intrinsic; Non-hydrate: 0 to 95%-0% RH; Temperature: 25° C.; Hydrate: 40 to 95%-0% RH; Temperature: 25° C.

Infra-red Spectrometry (IR) is the first analytical method used for the recognition and identification of crystalline substances. Due to different electrical environment of covalent bond in different crystal molecules, the covalent bond strength may change, and the change of covalent bond strength will inevitably lead to different IR spectra of different crystal forms.

In the present invention, the test parameters of IR are as follows: instrument model: Nicolet 6700 Fourier transform infrared spectrometer; single point ATR method with a resolution 4.0 $cm^{-1}$.

Raman Spectroscopy (RM) is a method of studying the molecular vibration based on the Raman effects. In contrast to the infrared absorption spectrum, the Raman Spectroscopy studies the frequency of the scattered light generated by the interaction of the molecule and the light. Non-polar groups, which generally have unobvious infrared absorption, have obvious Raman spectra absorption.

In the present invention, the test parameters of the RM are as follows: Instrument type: Thermo DXR Raman Microscope (confocal microscopy Raman spectrometer); laser wavelength: 532 nm; exposure time: 1.0 sec; exposure times: 10.

Example 1

Preparation of hydrochloride of (R)-methyl-2-(3-aminopiperidin-1-yl)-3-(2-cyanobenzyl)-4-carbonyl-3,4-dihydrothiophene [3, 2-d] pyrimidine-6-carboxylic acid (No. 1)

200 mg of (R)-methyl-2-(3-aminopiperidin-1-yl)-3-(2-cyanobenzyl)-4-carbonyl-3,4-dihydrothiophene[3, 2-d]pyrimidine-6-carboxylic acid was dissolved in solvent, THF-MeOH (1:1, v/v), and an identical equivalent of hydrochloric acid was added [(concentration 0.02 M, solvent THF-MeOH (1:1, v/v))], the solution obtained above was allowed to stand for 1 h at 40° C., and the crystals precipitated with stirring. The hydrochloride was obtained by filtering, and the hydrochloride was recrystallized by adding acetone-water (1:1, v/v). The obtained solid material was placed in a vacuum drying oven and dried for 70 hours under vacuum at 50° C., 5 KPa to obtain 150 mg of (R)-methyl-2-(3-aminopiperidin-1-yl)-3-(2)-cyanobenzyl)-4-carbonyl-3,4-dihydrothiophene[3,2-d]pyrimidine-6-carboxylic acid hydrochloride.

Result

The hydrochloride prepared in Example 1 was subjected to tests, such as XRD, TGA, DSC, DVS, IR and Raman etc.

FIG. 1 is an XRD pattern of the hydrochloride of Example 1, and it can be seen from FIG. 1 that there are absorption peaks at 7.43°, 11.06°, 11.70°, 13.46°, 15.03°, 15.34°, 15.84°, 16.35°, 17.59°, 18.32°, 19.54°, 20.13°, 21.24°, 21.96°, 22.46°, 22.74°, 23.67°, 24.01°, 24.83°, 25.19°, 26.63°, 27.20°, 29.32°, 30.26°, 32.15° for the hydrochloride.

FIG. 2 is a TG diagram of the hydrochloride of Example 1, and it can be seen from FIG. 2 that the weight loss of the hydrochloride is 64.33% at 210-400° C.

FIG. 3 is a differential scanning calorimetry (DSC) analysis spectrum of the hydrochloride of Example 1, and it can be seen from FIG. 3 that there is no melting peak prior to decomposition for the hydrochloride.

FIG. 4 is a hygroscopicity analysis (DVS) pattern of the hydrochloride of Example 1. It can be seen from FIG. 4 that the hydrochloride is slightly hygroscopic, and the humidity variation range is small (less than 3.0%) in the conventional storage humidity range. It absorbs 2.54% of water at 80% RH.

FIG. 5 is an infrared spectrum (IR) diagram of the hydrochloride of Example 1, and it can be seen from FIG. 5 that there are characteristic absorption peaks at 3429, 2951, 2827, 2225, 1720, 1687, 1560, 1533, 1446, 1385, 1261, 1064, 771 $cm^{-1}$ for the hydrochloride.

Example 2

Preparation of maleate of (R)-methyl-2-(3-aminopiperidin-1-yl)-3-(2-cyanobenzyl)-4-carbonyl-3,4-dihydrothiophene[3,2-d]pyrimidine-6-carboxylic acid (No. 2)

200 mg of (R)-methyl-2-(3-aminopiperidin-1-yl)-3-(2-cyanobenzyl)-4-carbonyl-3,4-dihydrothiophene[3, 2-d]pyrimidine-6-carboxylic acid was dissolved in solvent THF-MeOH (1:1, v/v), and an identical equivalent of maleic acid was added [(concentration 0.02 M, solvent THF-MeOH (1:1, v/v))], the solution obtained above was allowed to stand for 1 h at 40° C., and the crystals precipitated with stirring. The maleate was obtained by filtering, and the maleate was recrystallized by adding acetone-water (1:1, v/v). The obtained solid material was placed in a vacuum drying oven and dried for 70 hours under vacuum at 50° C., 5 KPa to obtain 170 mg of (R)-methyl-2-(3-aminopiperidin-1-yl)-3-(2)-cyanobenzyl)-4-carbonyl-3,4-dihydrothiophene[3,2-d]pyrimidine-6-carboxylic acid maleate.

Result

The maleate prepared in Example 2 was subjected to tests, such as XRD, TGA, DSC, DVS, IR and Raman etc.

FIG. 7 is an XRD pattern of the maleate of Example 2. It can be seen from FIG. 7 that there are absorption peaks at 7.550, 10.83°, 12.41°, 13.22°, 14.38°, 14.75°, 15.45°, 15.80°, 17.50°, 18.30°, 19.40°, 20.43°, 20.89°, 21.85°, 22.87°, 23.25°, 25.04°, 26.59°, 26.93°, 27.10°, 28.21°, 30.53°, 32.96° for the maleate.

FIG. 8 is a TG diagram of the maleate of Example 2. It can be seen from FIG. 8 that the weight loss of the maleate is 42.56% at 210-400° C.

FIG. 9 is a differential scanning calorimetry (DSC) analysis spectrum of the maleate of Example 2. It can be seen from FIG. 9 that the corresponding DSC of the maleate shows a melting point of 113.80° C.

FIG. 10 is a hygroscopicity analysis (DVS) pattern of the maleate of Example 2. It can be seen from FIG. 10 that the maleate has a slightly hygroscopicity, and the humidity variation range is small (less than 2.0%) in the conventional storage humidity range. It absorbs 1.57% of water at 80% RH.

FIG. 11 is an infrared spectrum (IR) diagram of the maleate of Example 2. It can be seen from FIG. 11 that there are characteristic absorption peaks at 3429, 3062, 2954, 2862, 2224, 1720, 1676, 1558, 1531, 1469, 1354, 1290, 1219, 1063, 864, 775, 654 $cm^{-1}$ for the maleate.

Example 3

Preparation of phosphate of (R)-methyl-2-(3-aminopiperidin-1-yl)-3-(2-cyanobenzyl)-4-carbonyl-3,4-dihydrothiophene[3,2-d]pyrimidine-6-carboxylic acid (No. 3)

200 mg of (R)-methyl-2-(3-aminopiperidin-1-yl)-3-(2-cyanobenzyl)-4-carbonyl-3,4-dihydrothiophene[3, 2-d]pyrimidine-6-carboxylic acid was dissolved in solvent THF-MeOH (1:1, v/v), and an identical equivalent of phosphoric acid was added [(concentration 0.02 M, solvent THF-MeOH (1:1, v/v))], the solution obtained above was allowed to stand for 1 h at 40° C., and the crystals precipitated with stirring. The phosphate was obtained by filtering, and the phosphate was recrystallized by adding acetone-water (1:1, v/v). The obtained solid material was placed in a vacuum drying oven and dried for 70 hours under vacuum at 50° C., 5 KPa to obtain 152 mg of (R)-methyl-2-(3-aminopiperidin-1-yl)-3-(2-cyanobenzyl)-4-carbonyl-3,4-dihydrothiophene[3,2-d]pyrimidine-6-carboxylic acid phosphate.

Result

The phosphate prepared in Example 3 was subjected to tests, such as XRD, TGA, DSC, DVS, IR and Raman etc.

FIG. 13 is an XRD pattern of the phosphate of Example 3, and it can be seen from FIG. 13 that there are absorption peaks at 6.230, 11.99°, 12.20°, 14.80°, 15.16°, 16.04°, 16.56°, 17.90°, 20.11°, 20.46°, 22.74°, 23.15°, 24.18°, 24.68°, 25.63°, 26.15° for the phosphate.

FIG. 14 is a TG diagram of the phosphate of Example 3, and it can be seen from FIG. 14 that the weight loss of the phosphate is 47.57% at 210-400° C.

FIG. 15 is a differential scanning calorimetry (DSC) analysis spectrum of the phosphate of Example 3. It can be seen from FIG. 15 that the corresponding DSC of the phosphate shows a melting point of 154.80° C.

FIG. 16 is a hygroscopicity analysis (DVS) pattern of the phosphate of Example 3. It can be seen from FIG. 16 that the phosphate is slightly hygroscopic, and the humidity variation range is small in the conventional storage humidity range.

FIG. 17 is an infrared spectrum (IR) diagram of the phosphate of Example 3. It can be seen from FIG. 17 that there are characteristic absorption peaks at 3408, 2951, 2860, 2225, 1716, 1684, 1601, 1556, 1531, 1450, 1379, 1282, 1238, 1124, 1064, 947, 868, 758, 521 $cm^{-1}$ for the phosphate.

Example 4

Preparation of glycolate of (R)-methyl-2-(3-aminopiperidin-1-yl)-3-(2-cyanobenzyl)-4-carbonyl-3,4-dihydrothiophene[3,2-d]pyrimidine-6-carboxylic acid (No. 4)

200 mg of (R)-methyl-2-(3-aminopiperidin-1-yl)-3-(2-cyanobenzyl)-4-carbonyl-3,4-dihydrothiophene[3, 2-d]pyrimidine-6-carboxylic acid was dissolved in solvent THF-MeOH (1:1, v/v), and an identical equivalent of glycolic acid was added [(concentration 0.02 M, solvent THF-MeOH (1:1, v/v))], the solution obtained above was allowed to stand for 1 h at 40° C., and the crystals precipitated with stirring. The glycolate was obtained by filtering, and the glycolate was recrystallized by adding acetone-water (1:1, v/v). The obtained solid material was placed in a vacuum drying oven and dried for 70 hours under vacuum at 50° C., 5 KPa to obtain 165 mg of (R)-methyl-2-(3-aminopiperidin-1-yl)-3-(2-cyanobenzyl)-4-carbonyl-3,4-dihydrothiophene[3,2-d]pyrimidine-6-carboxylic acid glycolate.

Result

The glycolate prepared in Example 4 was subjected to tests, such as XRD, TGA, DSC, DVS, IR and Raman etc.

FIG. 19 is an XRD pattern of the glycolate of Example 4. It can be seen from FIG. 19 that there are absorption peaks at 6.660, 8.92°, 9.91°, 10.20°, 13.35°, 13.92°, 15.78°, 16.71°, 16.89°, 17.41°, 18.70°, 19.37°, 20.12°, 20.51°, 21.22°, 21.78°, 22.75°, 23.00°, 23.87°, 24.08°, 24.37°, 25.52°, 26.55°, 27.02°, 27.48°, 28.23°, 28.63°, 28.84°, 29.68°, 30.14°, 30.51°, 31.41°, 31.76°, 33.00°, 33.81°, 34.13°, 35.21°, 35.83°, 36.37°, 37.70°, 37.93° for the glycolate.

FIG. 20 is a TG diagram of the glycolate of Example 4. It can be seen from FIG. 20 that the weight loss of the glycolate is 53.41% at 210-400° C.

FIG. 21 is a differential scanning calorimetry (DSC) analysis spectrum of the glycolate of Example 4, and it can be seen from FIG. 21 that the corresponding DSC of the glycolate shows a melting point of 188.75° C.

FIG. 22 is a hygroscopicity analysis (DVS) pattern of the glycolate of Example 4. It can be seen from FIG. 22 that the glycolate is slightly hygroscopic, and the humidity variation range is small (less than 2.0%) in the conventional storage humidity range. It absorbs 1.23% of water at 80% RH.

FIG. 23 is an infrared spectrum (IR) diagram of the glycolate of Example 4. It can be seen from FIG. 23 that there are characteristic absorption peaks at 3462, 2958, 2837, 2227, 1720, 1674, 1558, 1533, 1450, 1350, 1282, 1223, 1072, 928, 760, 692 $cm^{-1}$ for the glycolate.

All literatures mentioned in the present invention are incorporated by reference herein, as though individually incorporated by reference. Additionally, it should be understood that after reading the above teaching, many variations and modifications may be made by the skilled in the art, and these equivalents also fall within the scope as defined by the appended claims.

The invention claimed is:

1. A salt form of a compound of formula I, characterized in that the salt form is selected from the group consisting of hydrochloride, maleate, phosphate and glycolate

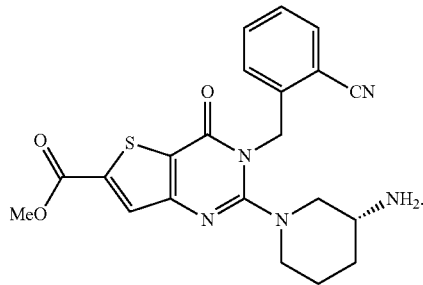

I

2. The salt form of claim 1 wherein the salt form is a crystal.

3. The salt form of claim 1 wherein the hydrochloride has one or more characteristics selected from the group consisting of:
   (1) the hydrochloride is a crystal; and/or
   (2) the X-ray powder diffraction pattern of the hydrochloride crystal includes 3 or more 2θ values selected from the group consisting of: 7.43±0.2°, 11.06±0.2°, 11.70±0.2°, 13.46±0.2°, 15.03±0.2°, 15.34±0.2°, 18.32±0.2°, 21.96±0.2°, 24.01±0.2°, 27.20±0.2°, 29.32±0.2°, 30.26±0.2°; and/or
   (3) in the differential scanning calorimetry analysis spectrum (DSC spectrum) of the hydrochloride crystal, there is no melting peak before decomposition; and/or
   (4) in the TG diagram of the hydrochloride crystal, there is a characteristic absorption peak at 272±2° C.; and/or
   (5) the thermal weight loss of the hydrochloride crystal is 64-65wt % at 400° C.; and/or
   (6) the weight gain of the hydrochloride crystal is calculated to be ≤3%, preferably ≤1%, more preferably ≤0.3%, after being placed in a desiccator having a humidity of 50% for 24 hours and taken out; and/or
   (7) the IR pattern of the hydrochloride crystal includes three or more characteristic absorption peaks represented by the wavelength λ, selected from the group consisting of: 3429±2 $cm^{-1}$, 2951±2 $cm^{-1}$, 2827±2 $cm^{-1}$, 2225±2 $cm^{-1}$, 1720±2 $cm^{-1}$, 1687±2 $cm^{-1}$, 1560±2 $cm^{-1}$, 1533±2$cm^{-1}$, 1446±2 $cm^{-1}$, 1385±2 $cm^{-1}$, 1261±2 $cm^{-1}$, 1064±2 $cm^{-1}$, 771±2 $cm^{-1}$.

4. The salt form of claim 1 wherein the maleate has one or more characteristics selected from the group consisting of:
   (1) the maleate is a crystal; and/or
   (2) the X-ray powder diffraction pattern of the maleate crystal includes 3 or more 2θ values selected from the group consisting of: 7.55±0.2°, 12.41±0.2°, 15.45±0.2°, 17.50±0.2°, 20.89 ±0.2°, 26.59 ±0.2°, 26.93 ±0.2°; and/or
   (3) in the differential scanning calorimetry analysis spectrum (DSC spectrum) of the maleate crystal, there is a characteristic absorption peak at 113±5° C.; and/or
   (4) the TG diagram of the maleate crystal includes characteristic absorption peaks selected from the group consisting of 77±2° C., 180±5° C., 284±5° C.; and/or
   (5) the thermal weight loss of the maleate crystal is 42-43wt % at 400° C.; and/or
   (6) the starting value of the endothermic transition temperature of the maleate crystal is 110±2° C.; and/or
   (7) the weight gain of the maleate crystal is calculated to be ≤3%, preferably ≤1%, more preferably ≤0.3%, after placed in a desiccator having a humidity of 50% for 24 hours and taken out; and/or (8) the IR pattern of the maleate includes three or more characteristic absorption peaks represented by the wavelength λ, selected from the group consisting of: 3429±2 cm$^{-1}$, 3062±2 cm$^{-1}$, 2954±2 cm$^{-1}$, 2862±2 cm$^{-1}$, 2224±2 cm$^{-1}$, 1720±2 cm$^{-1}$, 1676±2 cm$^{-1}$, 1558±2 cm$^{-1}$, 1531±2 cm$^{-1}$, 1469±2 cm$^{-1}$, 1354±2cm$^{-1}$, 1290±2 cm$^{-1}$, 1219±2 cm$^{-1}$, 1063±2 cm$^{-1}$, 864±2 cm$^{-1}$, 775±2 cm$^{-1}$, 654±2 cm$^{-1}$.

5. The salt form of claim 1 wherein the phosphate has one or more characteristics selected from the group consisting of:

(1) the phosphate is a crystal; and/or (2) the X-ray powder diffraction pattern of the phosphate crystal includes 3 or more 2θ values selected from the group consisting of: 11.99±0.2°, 12.20±0.2°, 14.80±0.2°, 20.11±0.2°, 20.46±0.2°, 24.18±0.2°, 24.68±0.2°; and/or (3) in the differential scanning calorimetry analysis spectrum (DSC spectrum) of the phosphate crystal, there is a characteristic absorption peak at 155±5° C.; and/or (4) in the TG pattern of the phosphate crystal, there is a characteristic absorption peak at 361±2° C.; and/or (5) the thermal weight loss of the phosphate crystal is 47-48 wt % at 400° C.; and/or (6) the starting value of the endothermic transition temperature of the phosphate crystal is 148±2° C.; and/or (7) the weight gain of the phosphate crystal is calculated to be ≤3%, preferably ≤1%, more preferably ≤0.3%, after being placed in a desiccator having a humidity of 50% for 24 hours and taken out; and/or (8) the IR pattern of the phosphate crystal includes three or more characteristic absorption peaks represented by the wavelength λ, selected from the group consisting of: 3408±2 cm$^{-1}$, 2951±2 cm$^{-1}$, 2860±2 cm$^{-1}$, 2225±2 cm$^{-1}$, 1716±2 cm$^{-1}$, 1684±2 cm$^{-1}$, 1601±2 cm$^{-1}$, 1556±2 cm$^{-1}$, 1531±2 cm$^{-1}$, 1450±2 cm$^{-1}$, 1379±2 cm$^{-1}$, 1282±2 cm$^{-1}$, 1238±2 cm$^{-1}$, 1124±2 cm$^{-1}$, 1064±2 cm$^{-1}$, 947±2 cm$^{-1}$, 868±2 cm$^{-1}$, 758±2 cm$^{-1}$, 521±2 cm$^{-1}$.

6. The salt form of claim 1 wherein the glycolate has one or more characteristics selected from the group consisting of:

(1) the glycolate is a crystal; and/or (2) the X-ray powder diffraction pattern of the glycolate crystal includes 3 or more 2θ values selected from the group consisting of: 8.92±0.2°, 10.20±0.2°, 13.35±0.2°, 16.89±0.2°, 19.37±0.2°; and/or (3) in the differential scanning calorimetry analysis spectrum (DSC spectrum) of the glycolate crystal, there is a characteristic absorption peak at 189±5° C.; and/or (4) the starting value of the endothermic transition temperature of the glycolate crystal is 148±2° C.; and/or (5) in the TG pattern of the glycolate crystal, there is a characteristic absorption peak at 192±2° C., 268±2° C.; and/or (6) the thermal weight loss of the glycolate crystal is 53-54 wt % at 400° C.; and/or (7) the weight gain of the glycolate crystal is calculated to be ≤3%, preferably ≤1%, more preferably ≤0.3%, after being placed in a desiccator having a humidity of 50% for 24 hours and taken out; and/or (8) the IR pattern of the glycolate crystal includes three or more characteristic absorption peaks represented by the wavelength λ, selected from the group consisting of: 3462±2 cm$^{-1}$, 2958±2 cm$^{-1}$, 2837±2 cm$^{-1}$, 2227±2 cm$^{-1}$, 1720±2 cm$^{-1}$, 1674±2 cm$^{-1}$, 1558±2 cm$^{-1}$, 1533±2cm$^{-1}$, 1450±2 cm$^{-1}$, 1350±2 cm$^{-1}$, 1282±2 cm$^{-1}$, 1223±2 cm$^{-1}$, 1072±2 cm$^{-1}$, 928±2 cm$^{-1}$, 760±2 cm$^{-1}$, 692±2cm$^{-1}$.

7. A method for preparing a salt form of a compound of formula I according to claim 1, characterized in that the method comprises the following steps of:

(1) a free base of the compound of formula I is dissolved in a solvent and a certain amount of acid is added;

(2) the solution obtained in step (1) is allowed to stand for a certain period of time to carry out a reaction at a certain temperature, and crystals are crystallized under stirring to obtain solids;

(3) the solids obtained in step (2) are filtered and/or dried to obtain the salt form according to claim 1.

8. The method of claim 7, wherein the alcohol is a C1-C10 alcohol.

9. A pharmaceutical composition, characterized in that the pharmaceutical composition comprises (1) the hydrochloride, the maleate, the phosphate, or the glycolate of the compound of formula I according to claim 1, or a combination thereof; and (2) a pharmaceutically acceptable excipient.

10. A method for treating type II diabetes mellitus and/or complications of type II diabetes mellitus, comprising administering to a patient a therapeutically effective amount of the pharmaceutical composition according of claim 9.

11. A pharmaceutical composition comprising the hydrochloride of claim 3 and a pharmaceutically acceptable excipient.

12. A pharmaceutical composition comprising the maleate of claim 4 and a pharmaceutically acceptable excipient.

13. A pharmaceutical composition comprising the phosphate of claim 5 and a pharmaceutically acceptable excipient.

14. A pharmaceutical composition comprising the glycolate of claim 6 and a pharmaceutically acceptable excipient.

15. A method for treating type II diabetes mellitus and/or complications of type II diabetes mellitus, comprising administering to a patient a therapeutically effective amount of the pharmaceutical composition according of claim 11.

16. A method for treating type II diabetes mellitus and/or complications of type II diabetes mellitus, comprising administering to a patient a therapeutically effective amount of the pharmaceutical composition according of claim 12.

17. A method for treating type II diabetes mellitus and/or complications of type II diabetes mellitus, comprising administering to a patient a therapeutically effective amount of the pharmaceutical composition according of claim 13.

18. A method for treating type II diabetes mellitus and/or complications of type II diabetes mellitus, comprising administering to a patient a therapeutically effective amount of the pharmaceutical composition according of claim 14.

* * * * *